(12) United States Patent
Takahashi

(10) Patent No.: US 8,399,014 B2
(45) Date of Patent: Mar. 19, 2013

(54) PHYSIOLOGICALLY ACTIVE COMPLEX COMPRISING PROTAMINE AND/OR SALT THEREFOR AND AN ACIDIC MACROMOLECULAR SUBSTANCE, AND USE THEREOF

(75) Inventor: Yoshinori Takahashi, Ibaraki (JP)

(73) Assignee: Maruha Nichiro Foods, Inc. (JP)

( * ) Notice: Subject to any disclaimer, the term of this patent is extended or adjusted under 35 U.S.C. 154(b) by 346 days.

(21) Appl. No.: 12/647,049

(22) Filed: Dec. 24, 2009

(65) Prior Publication Data

US 2010/0160232 A1 Jun. 24, 2010

(30) Foreign Application Priority Data

Dec. 24, 2008 (JP) ................... 2008-326915
Nov. 6, 2009 (JP) ................... 2009-255542

(51) Int. Cl.
*A23L 1/305* (2006.01)
*A61K 38/02* (2006.01)
*A61K 47/36* (2006.01)
*A61K 47/42* (2006.01)

(52) U.S. Cl. ...... 424/439; 426/648; 514/7.4; 514/21.92; 514/974

(58) Field of Classification Search .................. None
See application file for complete search history.

(56) References Cited

U.S. PATENT DOCUMENTS

| 3,868,358 A * | 2/1975 | Jackson ................. 530/303 |
| 4,853,218 A * | 8/1989 | Yim et al. ................. 424/85.7 |
| 2004/0062718 A1* | 4/2004 | Edwards et al. ................. 424/46 |

FOREIGN PATENT DOCUMENTS

| JP | 61-219363 A | 9/1986 |
| JP | 2-56416 A | 2/1990 |
| JP | 3-284627 A | 12/1991 |
| JP | 5-328935 A | 12/1993 |
| JP | 5-339168 A | 12/1993 |
| JP | 6-153875 A | 6/1994 |
| JP | 2000-14331 A | 1/2000 |
| JP | 2002-29950 A | 1/2002 |
| JP | 2002-65177 A | 3/2002 |
| JP | 2002-363197 A | 12/2002 |
| JP | 2003-73284 A | 3/2003 |
| JP | 2003-116496 A | 4/2003 |
| JP | 2003-144094 A | 5/2003 |
| JP | 2003-164268 A | 6/2003 |
| JP | 2003-183166 A | 7/2003 |
| JP | 2004-261139 A | 9/2004 |
| JP | 2005-130756 A | 5/2005 |
| JP | 2005-255653 A | 9/2005 |
| JP | 2005-298484 A | 10/2005 |
| JP | 2006-45216 A | 2/2006 |
| JP | 2006-45217 A | 2/2006 |
| JP | 2006-101832 A | 4/2006 |
| JP | 2006-131618 A | 5/2006 |
| JP | 2006-280254 A | 10/2006 |
| JP | 2007-246413 A | 9/2007 |
| JP | 2008-61593 A | 3/2008 |
| JP | 2008-99677 A | 5/2008 |

OTHER PUBLICATIONS

Vigo et al. Follicle-Like Model by Granulosa Cell Encapsulation . . . Tissue Engineering. 2005, vol. 11, No. 5/6, pp. 709-714.*
Hoshino, Yosuke, et al.; The Suppresive Effect of Protamine from Chum Salmon Milt on Lipid Absorption in Humans, Journal of the Japanese Society for Food Science and Technology, 55 (8), 360-366 (2008).
Korn, Edward D., Clearing Factor, A Heparin-Activated Lipoprotein Lipase, I. Isolation and Characterization of the Enzyme From Normal Rat Heart, The Journal of Biological Chemistry, 215, 1-14 (1955).
Japanese Office Action for Japanese Application No. 2009-255542 dispatched Oct. 20, 2010 with English translation.

* cited by examiner

*Primary Examiner* — Jeffrey E Russel
(74) *Attorney, Agent, or Firm* — Cantor Colburn LLP

(57) ABSTRACT

To provide a method of reducing an intrinsic harsh/astringent taste of protamine and a protamine salt and effectively using a fat absorption suppressive effect of these.

A complex is formed by reacting at least one of acidic macromolecular substances, such as alginate and polyglutamate, and gum arabic which are capable of forming a complex reducing harsh/astringent taste and dissociating protamine having a lipase inhibitory activity by pepsin treatment, with protamine or a protamine salt.

30 Claims, 7 Drawing Sheets

A: Protamine
   No Treated under Gastric Condition
B: Alginate Complex
   No Treated under Gastric Condition
C: Protamine
   Treated under Gastric Condition
D: Alginate Complex
   Treated under Gastric Condition Concentration for Evaluation
0.25 μg/ml as Protamine

PHYSIOLOGICALLY ACTIVE COMPLEX COMPRISING PROTAMINE AND/OR SALT THEREFOR AND AN ACIDIC MACROMOLECULAR SUBSTANCE, AND USE THEREOF

BACKGROUND OF THE INVENTION

1. Field of the Invention

The present invention relates to a complex comprising protamine and/or a salt thereof, which is a basic protein and has an intrinsic and strong harsh/astringent taste, by providing protamine in the form of the complex to reduce such harsh/astringent taste for intake, so as to maintain the functions of protamine such as fat absorption suppressive effect. The present invention relates also to a method of producing the complex and the uses of the complex.

2. Description of the Related Art

Protamine is a basic protein binding to DNA in the sperm nucleus of vertebrate animals. Protamine is considered to play a role in protecting genetic information by compressing and protecting DNA. The amino acid sequence of protamine more or less varies depending upon the species. The amino acid sequence of protamine is characterized in that an arginine residue occupies two thirds of the amino acids of the entire sequence. Because of an antimicrobial action on general bacteria, protamine, which is mainly extracted from fish testis (milt), has been widely used as a food preservative or the like (Japanese Patent Application Laid-Open No. 61-219363). Furthermore, protamine is also used in the field of medicinal drugs such as a long-acting insulin preparation and an anti-heparin agent. Thus, protamine is highly needed as a natural material. Besides these, protamine has been reported to effectively reduce a bitter/harsh taste by adding it to a beverage containing a catechin (Japanese Patent Application Laid-Open Nos. 5-328935 and 6-153875) and to inhibit lipase, which is an enzyme involved in fat absorption (J. Biol. Chem. 215, 1-14 (1955) and Japanese Patent Application Laid-Open No. 05-339168).

Recently, as lifestyle changes, energy intake tends to increase and energy consumption is likely to decrease by a person. Particularly, in dietary life, an increase of fat intake becomes a problem in connection with an increase of obesity and lifestyle-related diseases. It has been confirmed that protamine exerts a fat absorption suppressive effect when it is orally taken in a dose of 0.5 g (the Journal of the Japanese Society for Food Science and Technology 55 (8), 360-366 (2008)). From this, it is expected that protamine intake can contribute to improving lifestyle.

However, since protamine has an intrinsic strong taste (harsh/astringent taste), it is very difficult to take protamine or a salt thereof per se in an effective dose. This is a problem. When protamine is used in food as an antimicrobial agent, the taste does not pose any problem since protamine effectively works in a small amount. However, as the protamine amount to be added increases, its intrinsic taste creates a problem.

For example, in the case where protamine and/or a salt thereof are added, in an appropriate amount of protamine, to a beverage in an attempt to mask harsh taste and bitter taste of a food containing saponin, tannin, limonin, catechin, caffeine, and so on, protamine chemically binds to them to generate an insoluble substance. However, it is known that as the added amount of protamine increases, an intrinsic harsh taste comes to be sensed (Japanese Patent Application Laid-Open Nos. 5-328935 and 6-153875). Actually, in order to take protamine in an amount sufficient to produce its functions such as fat absorption suppressive effect, the concentration of protamine that is taken must be increased. In this case, the strong taste becomes a problem and use of protamine as or in foods is virtually limited. From these, it has been expected to provide a material capable of reducing the intrinsic taste of protamine without damaging the functions such as fat absorption suppressive effect of protamine. Addition of raffinose has been proposed to improve the quality of taste of a nutritional supplementary food or a beverage composition containing protamine (Japanese Patent Application Laid-Open No. 2003-144094).

Until now, various methods have been proposed for reducing or harsh taste of beverages and foods. For example, in order to reduce the harsh taste derived from zinc and iron ions, the following materials etc. are known:

Hyaluronic acid (Japanese Patent Application Laid-Open No. 2002-29950)

A nucleic acid-related substance (Japanese Patent Application Laid-Open No. 2006-131618)

A carnitine (Japanese Patent Application Laid-Open Nos. 2005-255653 and 2005-298484)

A collagen peptide (Japanese Patent Application Laid-Open No. 2006-045216)

A polyglycerin fatty acid ester (Japanese Patent Application Laid-Open Nos. 2002-065177, 2003-073284, and 2006-045217)

A casein-derived basic protein (Japanese Patent Application Laid-Open No. 2007-246413)

Furthermore, as a technique for reducing harsh taste typically represented by the harsh taste derived from a polyphenol, addition of the following materials is proposed:

Cyclodextrin (Japanese Patent Application Laid-Open No. 2003-183166, etc.)

A sweetener (aspartame: Japanese Patent Application Laid-Open No. 2-056416, steviol glucoside: Japanese Patent Application Laid-Open No. 2003-164268, sucralose: Japanese Patent Application Laid-Open No. 2008-099677, etc.)

An oligosaccharide (Japanese Patent Application Laid-Open Nos. 2006-280254 and 2008-061593)

Moreover, a method of adding a stabilizer such as pectin and carboxymethyl cellulose by controlling pH is known in order to mask bitter and harsh taste derived from a soybean peptide (Japanese Patent Application Laid-Open No. 2004-261139).

Furthermore, alginic acid (Japanese Patent Application Laid-Open No. 2003-116496, claim 3) and a polyglutamic acid (Japanese Patent Application Laid-Open No. 2005-130756, claim 3) are known to be effective for masking harsh taste derived from a polyphenol.

However, no disclosures are made in any one of the methods how to reduce intrinsic harsh/astringent taste of a basic substance such as protamine while maintaining its functions.

SUMMARY OF THE INVENTION

An object of the present invention is to elucidate a problem in connection with an intrinsic taste (harsh/astringent taste) of protamine, and provide a complex useful for a food, which is applicable to various types of food products and capable of reducing the intrinsic taste so as to thereby render intake of protamine easily without resistance, while maintaining the functions of protamine, such as fat absorption suppressive effect, as it is, and also provide a method for producing the complex and uses thereof.

Protamine and a salt thereof are a basic protein having an arginine-rich sequence and an intrinsic taste (harsh/astringent taste), different from a hydrophobic amino acid having a general bitter taste and a peptide rich in the hydrophobic amino acid. The harsh/astringent taste is distinguished from five basic tastes (sweet, salty, sour, bitter and "umami" (tasty)) and is a taste (stimulus) accompanied by physical stimuli in the oral cavity. As a substance having a harsh/astringent taste, a polyphenol such as tannin and catechin is known. Protamine in milt or the like strongly binds to DNA to form a complex (nucleoprotein). Protamine in a nucleoprotein has no harsh/astringent taste but does not have a lipase inhibitory activity. When a nucleoprotein is orally administered in a human, a fat absorption suppressive effect is not exerted based on protamine (the Journal of the Japanese Society for Food Science and Technology 55 (8) 360-366 (2008)). Therefore, the potential of protamine in such from as a food material for preventing a lifestyle-related disease such as obesity is low.

The present inventors focused on the interaction between protamine and an acidic macromolecular substance or gum arabic used as a food material, for reducing the taste of protamine and a salt thereof. Focusing on a digestion mechanism in the case of oral intake, they evaluated the functions of the complex by an artificial gastric fluid treatment including pepsin (pepsin treatment), which is a model of the stomach as the digestive organ.

Furthermore, it is considered that since protamine is a basic protein constituted mainly of arginine, protamine and a salt thereof have the strong harsh/astringent taste. On the other hand, a nucleoprotein, which is a complex of protamine and DNA, is tasteless. Since DNA is an acid, DNA strongly binds to protamine serving as a base via an ionic bond. Therefore, it is conceivable that protamine does not dissociate in the oral cavity and no harsh/astringent taste is sensed. However, the nucleoprotein is stable due to a strong binding ability and thus, protamine does not dissociate from the nucleoprotein in the stomach. For this reason, protamine may not exert an inhibitory effect on lipase secreted from the pancreas, providing no fat absorption suppressive effect. As a result, it was presumed that, if a complex of protamine and a material can be formed, from which protamine does not dissociate in the oral-cavity conditions but dissociates in the gastric conditions, it would be possible to obtain a food material masking the harsh/astringent taste intrinsic to protamine and having a fat absorption suppressive effect.

Intensive studies have been made based on the aforementioned points. As a result, the present inventors have found that an acidic macromolecular substance or gum arabic are the materials capable of forming a complex with at least one of protamine and salts thereof, reducing the harsh/astringent taste and being decomposed by pepsin treatment, thereby exhibiting a lipase inhibitory activity derived from protamine. Based on the new finding, the present invention was accomplished.

A complex according to the present invention is a complex comprising at least one of protamine and salts thereof, and at least one of acidic macromolecular substances and gum arabic, which exhibits a lipase inhibitory activity based on protamine by pepsin treatment.

A method for producing a complex according to the present invention is a method for producing a complex comprising at least one of protamine and salts thereof, and at least one of acidic macromolecular substances and gum arabic, and exhibiting a lipase inhibitory activity based on protamine by pepsin treatment. The method includes forming a complex by mixing at least one of protamine and salts thereof, and at least one of acidic macromolecular substances and gum arabic in an aqueous medium.

A first aspect of the method according to the present invention includes use of one of acidic macromolecular substances and gum arabic in a food product containing at least one of protamine and salts thereof in order to reduce the harsh/astringent taste provided by at least one of protamine and the salts thereof.

A second aspect of the method according to the present invention includes use of at least one of acidic macromolecular substances and gum arabic in production of a food product containing at least one of protamine and salts thereof in order to reduce the harsh/astringent taste provided by at least one of protamine and the salts thereof.

The powder mixture of the present invention is a mixture of (A) a powder of at least one of protamine and salts thereof and (B) a powder of at least one of acidic macromolecular substances and gum arabic. The powder mixture can provide the complex comprising at least one of protamine and the salts thereof and at least one of the acidic macromolecular substances and gum arabic in an aqueous medium, and exhibiting a lipase inhibitory activity based on protamine by pepsin treatment.

A functional food product according to the present invention contains the complex as described above or the powder mixture as described above.

A fat absorption suppressant of the present invention contains the complex as described above or the powder mixture as described above as an active ingredient.

Since protamine and a salt thereof have an intrinsic harsh/astringent taste, they conventionally can be rarely taken in a required amount to bring their functions. In contrast, the present invention makes it possible to improve the taste of protamine while maintaining functions by forming a complex of at least one of protamine and salts thereof, and at least one of acidic macromolecular substances and gum arabic. Furthermore, the complex of the present invention can be formed by a simple method, in which (A) at least one of protamine and salts thereof and (B) at least one of acidic macromolecular substances and gum arabic are directly mixed in an aqueous medium. In addition to this, the complex can be easily separated because the complex is hardly to dissolve in water. Moreover, the complex obtained in the present invention has no nasty natures in odor, taste and color and thus easily taken from the mouth. Even if these two components, (A) at least one of protamine and salts thereof and (B) at least one of acidic macromolecular substances and gum arabic, are mixed in the form of powder, the same functional effect can be obtained.

Therefore, a formulation in a form of a composition containing the complex or the powder mixture according to the present invention can be widely used for at least one of the food products selected from the group consisting of: a beverage (e.g., a cold beverage (coffee, cocoa, juice, mineral drink, tea drink, etc.), a milk beverage, a lactic beverage, a yogurt beverage, a carbonated beverage and an alcoholic beverage (sake, whisky and wine, etc.)), a spread (custard cream, butter cream, peanut cream, chocolate cream, cheese cream, etc.), a paste (fruit paste, vegetable paste, sesame paste, seaweed paste, etc.), a western confectionery (chocolate, doughnut, pie, cream puff, eclair, muffin, waffle, gum, gummi candy, jelly, candy, cookie, cracker, biscuit, snack cake, cake, pudding, etc.), a Japanese confectionary (candy, rice cracker, Karintou, cubic rice cracker, rice dumpling, bean cake, Daifuku (rice cake stuffed with bean jam), bean rice-cake, rice cake, bean jam, steamed bun, sponge cake, boiled peas with honey and bean jam, bean jelly, etc.), an ice (ice cream, lollipop, sherbet, chipped ice, etc.), a retort pouch (curry, beef bowl, Donburi dish consisting of Happosai on top of rice, porridge of rice and vegetables, rice porridge, fermented soybean soup, soup, Chinese noodle, pan-fried noodle, meat sauce, boiled fish, grilled fish, meatball, hamburger steak, dim sum, items in an Oden pot, steamed rice with red beans, barbecued chicken, custard-like egg and vegetable dish steamed in a cup, etc.), a convenience food (instant Chinese noodle, instant Udon, instant buckwheat noodle, instant pan-fried noodle, instant Won-ton noodles, instant sweet red-bean soup, fermented soybean-soup base, powdery-soup base, powdery-juice base, pancake mixture, etc.), a bottled food, a canned food, a gelatinous food (jelly, agar, terrine, gelatinous drink, etc.), a seasoning (table salt, natural salt, soy sauce, sweet cooking rice wine, vinegar, sugar, honey, fermented soybean paste, dressing, seasoning mixture, sauce, mayonnaise, ketchup, dried food sprinkled over rice, seasoning soy sauce, noodle soup, soup base, Chinese soup bouillon, seasonings for Chinese dish (seasoning for bean-curd soup seasoned with red pepper, seasoning for Chinese stir-fry containing green peppers and meat), bouillon, sauce of the roasted meat, source for cool Shabushabu, curry roux, stew roux, etc.), a milk product (milk, cheese, yogurt, fresh cream, etc.), a processed fruit (jam, marmalade, fruit soaked in syrup, dried fruit, etc.), a processed vegetable (grated radish, grated yam, vegetable mixture, frozen spinach, etc.), a processed grain food (noodle, pasta, bread, rice-noodle, etc.), pickles (pickled radish, pickle seasoned with sake lees, Korean pickles, Fukujin pickles, pickled scallion, pickled Chinese cabbage, pickles in mustard, Shiba pickles, lightly-pickled vegetable, pickles, etc.), a seasoning for pickles (seasoning for instant pickles, seasoning for Korean pickles, etc.), a fish-meat product (sausage, fish minced and steamed, tubular fish meat, Hanpen, flake, etc.), a livestock product (ham, sausage, salami sausage, bacon, etc.), a food delicacy (dried cuttlefish piece, torn pieces of cod, fish guts pickled in salt of the sea urchin, fish guts pickled in salt of the cuttlefish, fish guts pickled in salt of the kite, dried leatherfish seasoned with sweet cooking rice wine, dried globefish seasoned with sweet cooking rice wine, smoked cuttlefish, salted entrails of the sea cucumber, etc.), a dry food (seasoned and dried layer seaweed, etc.), a prepared food (food dressed with sauce, deep-fried food, fry-up food, grilled food, boiled food and vinegared food, etc.), a frozen food (fried food, tempura, fried chicken, croquette, spring roll, fried pork cutlet, dim sum, fried rice, meat dumpling, Chinese noodle, pan-fried noodle, hamburger steak, fried or baked octopus, Japanese muffin, steamed meat bun, etc.) and a fat and oil food (salad oil, margarine, butter).

With respect to a functional food, a wide variety of uses of the formulation in a form of a composition containing the complex or the powder mixture according to the present invention can be expected, which include a healthy food, a nutritional supplementary food, a specially designated health food or a health-oriented food for adding a beverage and a food; and exertion of excellent effects can be expected in preventing, treating and improving a lifestyle-related disease such as obesity, hyperlipemia and arteriosclerosis. Furthermore, the preparation of the present invention can be provided also as a cosmetic and an unregulated drug.

BRIEF DESCRIPTION OF THE DRAWINGS

In FIG. 1, the symbols have the following meanings:
○: Almost no harsh and astringent tastes were recognized.
Δ: Harsh and astringent tastes were recognized, which were allowable.
X: Disagreeable harsh and astringent tastes were recognized.

DETAILED DESCRIPTION OF THE PREFERRED EMBODIMENTS

Figure 1:
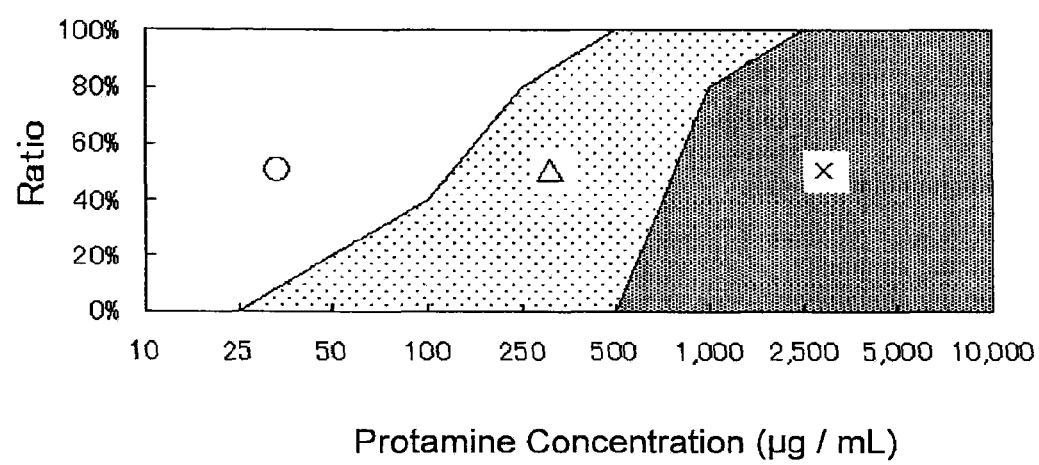
FIG. 1 is a graph showing the results of a study on concentration of protamine at which a harsh/astringent taste is sensed.

A complex according to the present invention can be obtained by reacting (A) at least one of protamine and salts thereof and (B) at least one of acidic macromolecular substances and gum arabic as materials to provide the complex. Any one of the acidic macromolecular substances and gum arabic available as a food material can be selected and used, which have the function of masking the harsh/astringent taste derived from arginines of protamine and capable of forming a complex having the aforementioned characteristics.

Protamine is principally prepared from a fish milt. The type of milt is not particularly limited. For example, milt of salmon (salmine), rainbow trout (ylidyne), herring (clupeine), mackerel (scombrin), sturgeon (sturine), tuna, cod, carp and perch are mentioned. In consideration of availability and cost etc., milt derived from salmon and herring are particularly preferred. Furthermore, an acid constituting a salt thereof can be selected depending upon the use of the salt. In consideration of uses in foods, cosmetics and pharmaceutical products, etc., the pharmaceutically acceptable salts mentioned below are preferred. As an acid addition salt, for example, a hydrochloride, a sulfate, a nitrate, methane sulfonate or p-toluene sulfonate; furthermore, a salt with a dicarboxylic acid such as oxalic acid, malonic acid, succinic acid, maleic acid or fumaric acid; moreover, a salt with a monocarboxylic acid such as acetic acid, propionic acid or butyric acid can be mentioned. In consideration of availability and cost, etc., a hydrochloride and a sulfate are particularly preferred.

As the acidic macromolecular substance, at least one selected from alginic acid and salts thereof, and a polyglutamic acid and a salt thereof is preferred.

Alginate is obtained from brown algae, such as kelp, blown (Wakame) seaweed, edible brown algae, *Ecklonia cava* and *Eisenia bicyclis*. As the alginate, one that can provide an effect of the present invention is selected and put in use. Alginate having a molecular weight exceeding 5000 is preferable, and furthermore, alginic acid or salts thereof having a molecular weight of at least 10,000 is further preferable. The upper limit of the molecular weight of alginate is not particularly limited. However, if the molecular weight is large, the viscosity of a solution increases and the solubility (of the solution) decreases, with the result that operability becomes worse. For this reason, the upper limit of the molecular weight of alginate is preferably about 2,000,000, and further preferably about 1,000,000. Furthermore, a base constituting a salt thereof is not particularly limited as long as it can form a complex having the aforementioned characteristics. However, in consideration of uses for foods, cosmetics and pharmaceutical products, bases constituting the pharmaceutically acceptable salts mentioned below are preferable. Examples of the salts include inorganic salts such as a sodium salt, a potassium salt, a calcium salt, a magnesium salt, an ammonium salt, a lithium salt and an aluminium salt; and organic salts including mono-, di- and tri-alkyl amine salts such as a methylamine salt, dimethylamine salt and a triethylamine salt, and mono-, di- and tri-hydroxyalkyl amine salts, a guanidine salt and an N-methyl glucosamine salt.

A polyglutamate is a polymer formed of glutamic acids, which are connected by an amide bond between an α-amino group and a y-carboxyl group. A polyglutamate has long been known as a component of a viscous substance of fermented soybean "Natto" and produced in a large amount by cultivation of bacteria belonging to the *Bacillus*. As the polyglutamic acid or a salt thereof to be used in the present invention, a polyglutamic acid or a salt thereof having a molecular weight exceeding 1,000 is preferable, and a polyglutamic acid or a salt thereof having a molecular weight of at least 10,000 is further preferable. The upper limit of molecular weight of the polyglutamic acid is not particularly limited. However, if the molecular weight is large, the viscosity of a solution increases and the solubility (of the solution) decreases, with the result that operability becomes worse. For this reason, the upper limit of a polyglutamic acid is preferably about 1,000,000. Furthermore, the base constituting a salt thereof is not particularly limited as long as it can form a complex having the aforementioned characteristics. However, in consideration of uses for foods, cosmetics, pharmaceutical products, bases constituting the pharmaceutically acceptable salts mentioned below are preferable. Examples of the salts include inorganic salts such as a sodium salt, a potassium salt, a calcium salt, a magnesium salt, an ammonium salt, a lithium salt and an aluminium salt; and organic salts including mono-, di- and tri-alkyl amine salts such as a methylamine salt, a dimethylamine salt and a triethylamine salt, and mono-, di- and tri-hydroxyalkyl amine salts, a guanidine salt and an N-methyl glucosamine salt.

Gum arabic is not particularly limited. For example, a salt of a polyuronic acid (arabic acid), etc. can be mentioned, whose main chain is formed of galactoses connected by a 1-3 bond and a side chain formed of arabinose, galactose, rhamnose and glucuronic acid is connected to carbon at the 6-position. Gum arabic having a molecular weight of about 200,000 to 250,000 can be preferably used.

The blending ratio of a complex-forming material(s) (B) (at least one of acidic macromolecular substances and gum arabic) relative to at least one of protamine and salts thereof (A) used in forming a complex is not particularly limited as long as the ratio can be properly set to form the complex. The weight ratio of (A):(B) is preferably set so as to fall within the range of 4:1 to 1:10.

Furthermore, when an acidic macromolecular substance is used as the complex-forming material (B), the weight ratio of (A):(B) is preferably set so as to fall within the range of 4:1 to 1:2. In other words, the ratio of at least one of the complex-forming materials (B) relative to at least one of protamine and the salts thereof (A) is preferably set to be 25 wt % to 200 wt %. In this case, further preferably, the ratio of at least one of the complex-forming materials (B) relative to at least one of protamine and the salts thereof (A) is set to be 50 wt % or more.

On the other hand, when gum arabic is used as the complex-forming material (B), the weight ratio of (A):(B) is preferably set so as to fall within the range of 1:2 to 1:10. In other words, the ratio of at least one of the complex-forming materials (B) relative to at least one of protamine and the salts thereof is preferably set to be 200 wt % to 1,000 wt %.

Furthermore, in the case of gum arabic, Gum arabic is preferably added in a ratio of 3:1 or more (300 wt % or more relative to protamine).

A complex according to the present invention can be produced by mixing (A) at least one of protamine and the salt thereof and (B) a complex-forming material(s) in an aqueous medium, followed by reacting them. More specifically, a complex can be easily produced by mixing an aqueous solution containing (A) at least one of protamine and the salts thereof and an aqueous medium containing (B) a complex-forming material(s). The concentration of protamine and a salt thereof and the concentration of a complex-forming material in an aqueous medium can be appropriately controlled and are not (particularly) limited; however, usually controlled preferably within the range of 0.1 wt % to 20 wt %. The aqueous medium to be used for the production is not particularly limited as long as it allows formation of a salt capable of forming a complex having the aforementioned characteristics. In consideration of uses for foods, cosmetics and pharmaceutical products, water, distilled water, deionized water, physiological saline solution, acidic water, basic water, buffer solution and alcohol water, etc. can be used. Examples of the acidic water may include an aqueous solution containing at least one of organic acids such as citric acid, malic acid, acetic acid, propionic acid, butyric acid, lactic acid, formic acid, tartaric acid, maleic acid, oxalic acid, succinic acid, ascorbic acid, gluconic acid, carboxylic acid, phthalic acid, trifluoroacetic acid, morpholinoethane sulfonic acid, 2-[4-(2-hydroxyethyl)-1-piperazinyl]ethane sulfonic acid and salts thereof; and inorganic acids such as hydrochloric acid, perchloric acid, carbonic acid and salts thereof. Furthermore, examples of the basic water may include an aqueous solution containing at least one of organic bases such as tris(hydroxymethyl), aminomethane, ammonia and salts thereof and inorganic bases such as sodium phosphate, potassium phosphate, calcium hydroxide, sodium hydroxide, potassium hydroxide, magnesium hydroxide, trisodium citrate, tripotassium citrate, sodium carbonate, potassium carbonate, sodium hydrogen carbonate and potassium hydrogen carbonate. Furthermore, as the buffer solution, a citric acid buffer solution, a phosphate buffer solution, an acetic acid buffer solution and a tris hydrochloric acid buffer solution and the like can be selected depending upon the pH suitable for use. The concentrations of an acid, a base and a buffer solution constituting the aqueous medium are preferably 0.001 wt % to 1 wt %, and more preferably 0.01 wt % to 0.5 wt % at which taste is not largely affected. Furthermore, the pH of a basic aqueous medium is preferably 8 or more, more preferably 8 to 12, and further preferably 9 to 11. If pH is excessively large, hydrolysis may possibly occur and care must be taken in handling. For the reason, pH preferably falls within the aforementioned range. The pH of the acidic aqueous medium is preferably less than 8, more preferably 2.0 to 7.5, and further preferably 2.5 to 5. If pH is low, bacterial growth can be suppressed in the absence of an antiseptic agent. For the reason, the aforementioned range is preferable. Furthermore, specific examples of alcohol to be used in the alcohol water include a monovalent alcohol such as methanol, ethanol, propanol and butanol, and a polyhydric alcohol such as propylene glycol and glycerol. In consideration of safety at the time of oral intake of the complex produced, ethanol is preferably used. The water content of the alcohol water is preferably 60 wt % or less, and more preferably 40 wt % or less. The temperature of individual aqueous mediums is not limited; however, preferably, 0° C. to 80° C., more preferably, 5° C. to 60° C., and further preferably 15° C. to 40° C.

A complex according to the present invention is poorly soluble in water and can be obtained in the dispersion state in an aqueous medium or as a precipitate. The complex thus obtained is, if necessary, recovered from the aqueous medium, desalted and then dried. In this way, a complex product can be obtained. The complex can be desalted by washing with water, thereby reducing the salt component contained in the complex to a desired concentration.

Furthermore, if necessary, a dispersant can be added to an aqueous medium to maintain an emulsion state or a dispersion state of the complex produced in the aqueous medium. The dispersant is not particularly limited; however, for example, a water-soluble soybean polysaccharide, propylene glycol alginate, pectin, carboxymethylcellulose (CMC) or a salt thereof, microcrystalline cellulose, fermented cellulose, carrageenan (iota, lambda, kappa), xanthan gum, gum arabic, guar gum, locust bean gum, tamarind seed gum, gum Ghatti, Macrophomopsis gum, Tara gum, Gellan gum and the like can be used. The addition amount of dispersant is generally selected from the range of 0.001 wt % to 1 wt % relative to the total amount of solution, and more preferably, 0.1 wt % to 1 wt %. The dispersant may be added when a beverage is produced using a complex in order to attain dispersion stability of the complex. The blending ratio at this time is generally selected from the range of 0.01 wt % to 10 wt % relative to the total amount of beverage, and more preferably, 0.05 wt % to 5 wt %. Furthermore, the pH of the aqueous medium for the emulsion or the dispersion is preferably selected from the range of 2.5 to 8.5.

Accordingly, a complex according to the present invention can be provided in various forms such as a milky lotion, a dispersion solution, slurry and a dried material.

It is noted that, when a dispersant is used, the dispersant is preferably present during the formation of a complex. For example, the following methods may be mentioned, which are preferably used alone or in combination with two types or more of the following methods in which the complex-forming material is at least one of the acidic macromolecular substances and gum arabic:

(1) At least one of protamine and salts thereof and a dispersant are mixed in an aqueous medium. To this, a complex-forming material(s) (or an aqueous medium solution thereof) is added.

(2) A complex-forming material(s) and a dispersant are mixed in an aqueous medium. To this, at least one of protamine and salts thereof (or an aqueous medium solution thereof) is added.

(3) At least one of protamine and salts thereof and a dispersant (both are in powder form) are mixed to form a solid mixture. The mixture is added to an aqueous medium solution of a complex-forming material(s).

(4) A complex-forming material(s) and a dispersant (both are in powder form) are mixed to form a solid mixture. The mixture is added to an aqueous medium solution of at least one of protamine and salts thereof.

(5) A dispersant is previously added to an aqueous medium. To this, at least one of protamine and salts thereof (or an aqueous medium solution thereof) and a complex-forming material(s) (or an aqueous medium solution thereof) are added.

(6) At least one of protamine and salts thereof, complex-forming material(s) and a dispersant (all are in powder form) are mixed to form a solid mixture. The mixture is added to an aqueous medium solution.

When a complex according to the present invention is decomposed by gastric condition, protamine is liberated and shows a lipase inhibitory activity. More specifically, when a complex according to the present invention is orally taken and then decomposed in the stomach, a fat absorption suppressive effect can be produced. Therefore, use of a complex according to the present invention makes it possible to provide a composition, food and pharmaceutical product reduced in harsh/astringent taste derived from protamine and a salt thereof and having a fat absorption suppressive effect.

On the other hand, when a complex is formed of a food (or a food material) containing at least one of protamine and salts thereof and an acidic macromolecular substance(s), it is possible to reduce the harsh/astringent taste derived from these substances. Accordingly, if such a complex is formed in a food (or food material) by adding a complex-forming material(s) to a food (or food material) containing at least one of protamine and salts thereof or by adding a complex-forming material(s) in any stage of the production process for the food containing at least one of protamine and salts thereof, it is possible to reduce the harsh/astringent taste derived from at least one of protamine and the salts thereof.

Furthermore, if such a complex is formed in a food (or food material) by adding a food (or food material) containing an acidic macromolecular substance(s) to the other food (or the other food material) containing at least one of protamine and salts thereof, or by adding a food (or food material) containing a complex-forming material(s) in any stage of the production process for the other food (or the other food material) containing at least one of protamine and salts thereof, it is possible to reduce the harsh/astringent taste derived from at least one of protamine and the salts thereof.

As a food (or food material) containing an acidic macromolecular substance(s) as a complex-forming material, for example, a food containing brown algae (kelp, blown (Wakame) seaweed, edible brown algae, *Ecklonia cava* and *Eisenia bicyclis*, etc.), which contains alginate, and a fermented soybean product containing a polyglutamate are mentioned.

On the other hand, at least one of protamine and salts thereof and a complex-forming material(s) in the form of powder are mixed to form a powder mixture, which is to be used as a raw material for producing a complex as mentioned above or used as a powder mixture for forming the complex in various products such as a food (or food material). When the powder mixture is orally taken as a fat absorption suppressant, etc. the mixture can form a complex as mentioned above with the help of moisture (the saliva and water additionally taken) of the oral cavity.

In producing a powder mixture, the blending ratio of at least one of protamine and salts thereof and a complex-forming material is as follows. The ratio of at least one of the complex-forming materials is preferably set to be 25 wt % to 200 wt % relative to at least one of protamine and the salts thereof. Furthermore, the ratio of at least one of the complex-forming materials is more preferably set to be 50 wt % or more relative to at least one of protamine and the salts thereof.

The particle sizes of powders of at least one of protamine and salts thereof and a complex-forming material(s) preferably may range within the range of 1 μm to 1,000 μm.

Also, a dispersant as mentioned above can be contained to the powder mixture, if necessary. If a dispersant is previously added to a powder mixture likewise, a complex, which is formed when the powder mixture is added to an aqueous medium, can be satisfactorily dispersed in the aqueous medium without precipitating. To avoid a precipitate, a dispersant is particularly preferably used when a powder mixture is directly added to a liquid-state food, a liquid food and a beverage, etc. Furthermore, if a dispersant is previously added to a powder mixture, a dispersion solution of a complex, which is obtained when the powder mixture is added to an aqueous medium, can get an advantage: when the dispersion solution is added to a food or a food material, it can be uniformly added with good operability.

Furthermore, the powder mixture containing a dispersant can be added to an aqueous medium and used as a liquid-state fat absorption suppressant to be orally administered. Furthermore, when a powder mixture is directly administered through the mouth, if the mixture contains a dispersant, it is possible to suppress generation of a precipitate in the mouth. As a result, the powder mixture can be used without discomfort feeling.

The content of a dispersant in a powder mixture is selected from the range of 0.1 wt % to 100 wt % relative to the total amount of powder mixture, more preferably, 1 wt % to 50 wt %, and further preferably 5 wt % to 25 wt %.

EXAMPLES

The present invention will be more specifically described by way of examples. The present invention can be modified as long as it does not deviate from the scope of the invention and is not limited to the examples.

Example 1

Study on Concentration of Protamine at which the Harsh/Astringent Taste is Sensed Investigation was made on the threshold of protamine concentration at which a harsh/astringent taste was sensed when protamine was orally taken.

Materials Used:
Protamine: Proserve manufactured by Maruha Nichiro Foods, Inc.

Protamine (0.8 g) was dissolved in distilled water (40 mL) to prepare a 20,000 μg/mL aqueous protamine solution. The solution was sequentially diluted with distilled water to obtain 10 types protamine solutions different in concentration (10,000, 5,000, 2,500, 1,000, 500, 250, 100, 50, 25 and 10 μg/mL). An aliquot (0.5 mL) was taken from the aqueous solutions sequentially in the ascending order of concentration and evaluated for harsh/astringent taste on a scale of one to three. The results are shown in FIG. 1.

The concentration of protamine at which the harsh/astringent taste of protamine was sensed varies depending upon the persons as the panelists; however, some persons sensed the taste first at 50 to 250 μg/mL and all persons sensed the taste at 500 μg/mL. Furthermore, it was found that 80% of the total persons had a feeling of discomfort at 1,000 μg/mL. It is noted that, in order for a person as a subject requiring the effective amount of protamine (0.5 g), which produces a fat absorption suppressive effect, the person must take 1 L of 500 μg/mL protamine. Therefore, it was apparent that the taste of protamine must be improved to put it into practical use.

Example 2

Study on Reducing the Harsh/Astringent Taste of Protamine

The standard dose of protamine per day for producing a fat absorption suppressive effect is 0.5 g. Assuming that protamine is applied to a beverage, a solution (50 mL) containing 0.5 g of protamine was prepared. Using the solution containing protamine in a concentration of 10 mg/mL, sensory test was performed to evaluate an effect of reducing the harsh/astringent taste.

Materials Used:
Protamine: Proserve manufactured by Maruha Nichiro Foods, Inc.

Polyglutamate: polyglutamic acid PGA manufactured by Yakult Pharmaceutical Industry Co., Ltd.
Glutamic acid: sodium glutamate manufactured by Cheil Jedang
Carrageenan: Genugel carrageenan type CJ manufactured by CP KELCO Japan
Pectin: Grindsted Pectin AMD 780 manufactured by Danisco Japan
Chondroitin sulfate: SCP-NB manufactured by Maruha Nichiro Foods, Inc.
Hyaluronic acid: sodium hyaluronate "Maruha" manufactured by Maruha Nichiro Foods, Inc.
Nucleic acid: DNA-Na manufactured by Maruha Nichiro Foods, Inc.
L-ascorbic acid: L-ascorbic acid manufactured by Nippon Bulk Yakuhin Co., Ltd.
Lecithin: Benecoat BMI-40 manufactured by Kao Corporation
Alginate: ULV-L3 manufactured by KIM ICA Corporation
Alginate oligosaccharide: NaAO manufactured by Maruha Nichiro Foods, Inc.
Malic acid: DL-malic acid manufactured by iPROS corporation
Citric acid: citric acid (anhydride) fine particles manufactured by San-Ei Gen F.F.I., Inc.

Method for Preparing Evaluation Solution:

Protamine (10 g) was dissolved in distilled water (500 mL) to prepare a 20 mg/mL aqueous protamine solution. On the other hand, each (2 g) of the test substances was dissolved in distilled water (100 mL) to prepare 20 mg/mL aqueous solutions of the test substances (the concentrations of carageenan and lecithin solutions were set to be 10 mg/mL, the concentration of a hyaluronic acid solution was set to be 2 mg/mL). To each (2 mL) of the test-substance solutions, the aqueous protamine solution (2 mL) was added and stirred. Some of the solution mixtures having a precipitate were subjected to centrifugation (3,000 rpm, 10 minutes). The supernatant and the precipitate were checked for the effect of reducing the harsh/astringent taste of protamine by a sensory test. The results obtained are shown in Table 1.

TABLE 1

The effect of material (test substance) on reducing the harsh/astringent taste of protamine

| Name of substance | Evaluation | Aqueous solution | Precipitate |
|---|---|---|---|
| Protamine | — | Strong astringent taste | — |
| Polyglutaminate | ⊚ | Tasteless (slightly salty) | Gum-like white substance |
| Sodium glutamate | | Slightly mitigated and Umami taste is strong | — |
| Carrageenan | Δ | Slightly mitigated and harsh taste remains | Fibrous white substance and not chewable |
| Pectin | Δ | Slightly mitigated and harsh taste remains | Tasteless, viscous white substance |
| Alginate | ⊚ | Tasteless (slightly salty) | Gum-like white substance |
| Alginate oligosaccharide | Δ | Slightly mitigated and harsh taste remains | Trace amount of white precipitate was observed |
| Chondroitin sulfate | X | No effect | — |
| Hyaluronic acid | X | No effect | — |
| Nucleic acid | ○ | Slightly mitigated but salty taste is strong | Powdery white substance with slight harsh taste |

TABLE 1-continued

The effect of material (test substance) on reducing the harsh/astringent taste of protamine

| Name of substance | Evaluation | Aqueous solution | Precipitate |
|---|---|---|---|
| Malic acid | X | No effect | — |
| Citric acid | X | No effect | — |
| L-ascorbic acid | Δ | Mitigated and harsh taste remains as aftertaste | — |
| Lecithin | Δ | Mitigated but stimulative | White turbidity |

Evaluation:
◎: Harsh/astringent taste is masked and rarely sensed,
○: Harsh/astringent taste is reduced but slightly remains,
Δ: Harsh/astringent taste is slightly masked,
X: No effect,
—: Blank.

Good results were obtained in polyglutamate and alginate. In either case, it was confirmed that a complex was formed and no taste was sensed. Polyglutamate is a polymer formed of glutamic acids, which are connected by an amide bond between an α-amino group and a γ-carboxyl group and is a viscous substance of fermented soybean. Since the monomer thereof, namely, sodium glutamate, produces no effect, it is considered that a substance having an effect of reducing the harsh/astringent taste of protamine must have a certain-size molecular weight. Alginate is a viscous component contained in seaweed such as kelp. In an alginate oligosaccharide, which is an oligomer having a molecular weight of about 2,000, no complex was formed and no effect of reducing the harsh/astringent taste was confirmed. In the case of a polymer having a molecular weight of 54,000, the polymer and protamine formed a complex and a satisfactory effect of reducing the harsh/astringent taste was confirmed. Also in other acidic macromolecular food materials such as carageenan and pectin, DNA reduced in molecular weight and lecithin, an effect of reducing the harsh/astringent taste of protamine was more or less confirmed; however, it was considered difficult to put them in practical use.

Example 3

Study on the Effect of Alginate on Reducing the Harsh/Astringent Taste of Protamine Materials used:
Protamine: Proserve manufactured by Maruha Nichiro Foods, Inc.
Alginate: ULV-L3 manufactured by KIM ICA Corporation
Protamine (2 g) was dissolved in distilled water (100 mL) to prepare a 20 mg/mL aqueous protamine solution. An aliquot of the solution was diluted with distilled water to prepare solutions (10, 5.0 and 2.86 mg/mL). Furthermore, alginate (4 g) was dissolved in distilled water (100 mL) to prepare a 40 mg/mL aqueous alginate solution. An aliquot of the solution was diluted with distilled water to prepare solutions (20, 15, 10, 7.5, 5.0, 2.5 and 1.0 mg/mL). When protamine of 10 mg/mL in concentration was evaluated (this is a concentration assuming that protamine (0.5 g) is taken from a beverage (50 mL)), a 20 mg/mL aqueous protamine solution (2 mL) was added to each (2 mL) of the aqueous alginate solutions different in concentration. When protamine of 5.0 mg/mL in concentration was evaluated (this is a concentration assuming that protamine (0.5 g) is taken from a beverage (100 mL)), a 10 mg/mL aqueous protamine solution (2 mL) was added to each (1 mL) of the aqueous alginate solutions different in concentration. When protamine of 2.5 mg/mL in concentration was evaluated (this is a concentration assuming that protamine (0.5 g) is taken from a beverage (200 mL)), a 5 mg/mL aqueous protamine solution (4 mL) was added to each (1 mL) of the aqueous alginate solutions different in concentration. When protamine of 1.43 mg/mL in concentration was evaluated (this is a concentration assuming that protamine (0.5 g) is taken from a beverage (350 mL)), a 2.86 mg/mL aqueous protamine solution (3.5 mL) was added to each (0.5 mL) of the aqueous alginate solutions different in concentration. These solutions were evaluated for the harsh/astringent taste by a sensory test. The results obtained are shown in Table 2.

TABLE 2

The effect of alginate on reducing the harsh/astringent taste of protamine

| | Concentration of alginate solution added (mg/mL) | | | | | | | |
|---|---|---|---|---|---|---|---|---|
| | 40 | 20 | 15 | 10 | 7.5 | 5.0 | 2.5 | 1.0 |
| | Ratio to protamine | | | | | | | |
| | 200% | 100% | 75% | 50% | 37.5% | 25% | 12.5% | 5% |
| Concentration of protamine evaluated: 10 mg/mL | ◎ | ◎ | ◎ | Δ | Δ | Δ | X | X |
| Concentration of protamine evaluated: 5.0 mg/mL | ◎ | ◎ | ◎ | ○ | Δ | Δ | Δ | X |
| Concentration of protamine evaluated: 2.5 mg/mL | ◎ | ◎ | ◎ | ◎ | ○ | ○ | Δ | X |
| Concentration of protamine evaluated: 1.43 mg/mL | ◎ | ◎ | ◎ | ◎ | ○ | ○ | Δ | Δ |

Evaluation:
◎: Harsh/astringent taste is masked and rarely sensed,
○: Harsh/astringent taste is reduced but slightly remains,
Δ: Harsh/astringent taste is slightly masked and slightly satisfactory,
X: No effect.

Until the addition amount of alginate reached 12.5 wt % (1:8) relative to an aqueous protamine solution of 10 mg/mL in concentration, an effect of reducing the harsh/astringent taste was not confirmed. When the addition amount increased to 25 wt % (1:4), the effect of reducing the harsh/astringent taste was first confirmed. Sufficient effect was confirmed in an addition amount of 37.5 wt % (3:8). Furthermore, when the addition amount reached 75 wt % (3:4), the harsh/astringent taste of protamine was not sensed at all. Furthermore, as the concentration of protamine decreased, even if the addition amount of alginate was low, the effect of reducing the harsh/astringent taste was confirmed.

Example 4

Study on the Effect of Polyglutamate on Reducing Harsh/Astringent Taste of Protamine Materials Used:
Protamine: Proserve manufactured by Maruha Nichiro Foods, Inc.
Polyglutamate: polyglutamic acid PGA manufactured by Yakult Pharmaceutical Industry Co., Ltd.

In the same manner as in Example 3, aqueous protamine solutions (20, 10, 5.0 and 2.86 mg/mL) and aqueous polyglutamate solutions (40, 20, 10, 7.5, 5.0, 2.5 and 1.0 mg/mL) were prepared. Thereafter, the solutions different in type were mixed to evaluate for the harsh/astringent taste by a sensory test. The results obtained are shown in Table 3.

TABLE 3

The effect of polyglutamate on reducing harsh/astringent taste of protamine

| | Concentration of polyglutamate solution added (mg/mL) | | | | | | | |
|---|---|---|---|---|---|---|---|---|
| | 40 | 20 | 15 | 10 | 7.5 | 5.0 | 2.5 | 1.0 |
| | Ratio to protamine | | | | | | | |
| | 200% | 100% | 75% | 50% | 37.5% | 25% | 12.5% | 5% |
| Concentration of protamine evaluated: 10 mg/mL | ◎ | ◎ | ◎ | ○ | Δ | Δ | X | X |
| Concentration of protamine evaluated: 5.0 mg/mL | ◎ | ◎ | ◎ | ○ | ○ | Δ | Δ | X |
| Concentration of protamine evaluated: 2.5 mg/mL | ◎ | ◎ | ◎ | ◎ | ○ | Δ | Δ | Δ |
| Concentration of protamine evaluated: 1.43 mg/mL | ◎ | ◎ | ◎ | ◎ | ◎ | ○ | Δ | Δ |

Evaluation:
◎: Harsh/astringent taste is masked and rarely sensed,
○: Harsh/astringent taste is reduced but slightly remains,
Δ: Harsh/astringent taste is slightly masked and slightly satisfactory,
X: No effect.

Until the addition amount of polyglutamate reached 12.5 wt % (1:8) relative to an aqueous protamine solution of 10 mg/mL in concentration, an effect of reducing the harsh/astringent taste was not observed. When the addition amount increased to 25 wt % (1:4), the effect of reducing the harsh/astringent taste was first confirmed. Sufficient effect was confirmed in an addition amount of 50 wt % (1:2). Furthermore, when the addition amount reached 50 wt % (3:4), the harsh/astringent taste of protamine was not sensed at all.

Example 5

Effect of Polyglutamate on Reducing the Harsh/Astringent Taste of Protamine Varied Depending Upon the Molecular Weight With respect to polyglutamate whose effect of reducing the harsh/astringent taste of protamine was confirmed, the effect varying depending upon the molecular weight was investigated.

Materials used:
Protamine: Proserve manufactured by Maruha Nichiro Foods, Inc.
Polyglutamate: polyglutamic acid PGA manufactured by Yakult Pharmaceutical Industry Co., Ltd.

Protamine (1.6 g) was dissolved in distilled water (80 mL) to prepare a 20 mg/mL aqueous protamine solution. Polyglutamate (2 g) was dissolved in distilled water (50 mL) to prepare a 40 mg/mL aqueous polyglutamate solution. Thereafter, the solution was diluted with distilled water to prepare solutions (40, 20, 15, 10, 7.5, 5.0, 2.5, 1.0 mg/mL). To each (2 mL) of the aqueous polyglutamate solutions different in concentration, the aqueous protamine solution (2 mL) was added and stirred to evaluate for the harsh/astringent taste by a sensory test. The results obtained are shown in Table 4.

TABLE 4

The effect of polyglutamate on reducing the harsh/astringent
taste of protamine varied depending upon the molecular weight

| | Ratio to protamine | | | | | | | |
|---|---|---|---|---|---|---|---|---|
| | 200% | 100% | 75% | 50% | 37.5% | 25% | 12.5% | 5% |
| | Concentration of substance added (mg/mL) | | | | | | | |
| | 40 | 20 | 15 | 10 | 7.5 | 5.0 | 2.5 | 1.0 |
| Type A (weight-average molecular weight: 878,000) | ⊚ | ⊚ | ⊚ | ⊚ | ○ | Δ | X | X |
| Type B (weight-average molecular weight: 81,000) | ⊚ | ⊚ | ⊚ | ○ | Δ | X | X | X |
| Type C (weight-average molecular weight: 150,000) | ⊚ | ⊚ | ⊚ | ○ | Δ | X | X | X |
| Type D (weight-average molecular weight: 11,000) | ⊚ | ⊚ | ⊚ | ○ | Δ | X | X | X |

Evaluation:
⊚: Harsh/astringent taste is masked and rarely sensed,
○: Harsh/astringent taste is reduced but slightly remains,
Δ: Harsh/astringent taste is slightly masked and slightly satisfactory,
X: No effect.

There was a tendency that the larger the molecular weight of polyglutamate, the stronger the effect of reducing the harsh/astringent taste of protamine. In type A having the largest molecular weight, the effect of reducing the taste was confirmed at an addition amount of 50 wt % (1:2) to protamine. However, in other types, taste was not virtually sensed at an addition amount of 75 wt % (3:4). At an addition amount of 50 wt % (1:2), harsh/astringent taste was likely to remain. In type A polymer, harsh/astringent taste was tolerable up to an addition amount of 25 wt % (1:4); whereas in other type polymers, up to 37.5 wt % (3:8).

Example 6

Effect of Alginate on Reducing the Harsh/Astringent Taste of Protamine Varied Depending Upon the Molecular Weight With respect to alginate whose effect of reducing the harsh/astringent taste of protamine was confirmed, the effect varying depending upon the molecular weight was investigated.

Materials Used:

Protamine: Proserve manufactured by Maruha Nichiro Foods, Inc.

Alginate: 1-8, IL-2, ULV-5, ULV-1, ULV-L3 manufactured by KIM ICA Corporation; alginate oligosaccharide NaAO manufactured by Maruha Nichiro Foods, Inc.

Protamine (1.6 g) was dissolved in distilled water (80 mL) to prepare a 20 mg/mL aqueous protamine solution. Furthermore, each (800 mg) of the alginates was dissolved in distilled water (20 mL) to prepare 40 mg/mL solutions. Thereafter, each solution was sequentially diluted with distilled water to obtain solutions (20, 15, 10, 7.5, 5 and 2.5 mg/mL). To each alginate solution (0.5 mL), the protamine solution (0.5 mL) was added and stirred, and centrifugation (10,000 rpm, 5 minutes) was performed. A precipitation was washed with distilled water (1 mL). The supernatant and precipitate of each solution were evaluated for the harsh/astringent taste by a sensory test. The results obtained are shown in Table 5.

TABLE 5

The effect of alginate on reducing the harsh/astringent taste
of protamine varied depending upon the molecular weight

| | | Ratio to protamine | | | | | | |
|---|---|---|---|---|---|---|---|---|
| | | 200% | 100% | 75% | 50% | 37.5% | 25% | 12.5% |
| | | Concentration of substance added (mg/mL) | | | | | | |
| | | 40 | 20 | 15 | 10 | 7.5 | 5.0 | 2.5 |
| Sodium alginate I-8 (weight-average molecular weight: 1,737,000) | Supernatant | ○ | ○ | Δ | X | X | X | X |
| | Precipitate | ⊚ | ⊚ | ⊚ | ⊚ | ⊚ | ⊚ | ⊚ |
| Sodium alginate IL-2 (weight-average molecular weight: 910,000) | Supernatant | ⊚ | ⊚ | ○ | Δ | X | X | X |
| | Precipitate | ⊚ | ⊚ | ⊚ | ⊚ | ⊚ | ⊚ | ⊚ |

TABLE 5-continued

The effect of alginate on reducing the harsh/astringent taste
of protamine varied depending upon the molecular weight

| | | Ratio to protamine | | | | | | |
|---|---|---|---|---|---|---|---|---|
| | | 200% | 100% | 75% | 50% | 37.5% | 25% | 12.5% |
| | | Concentration of substance added (mg/mL) | | | | | | |
| | | 40 | 20 | 15 | 10 | 7.5 | 5.0 | 2.5 |
| Sodium alginate ULV-5 (weight-average molecular weight: 138,000) | Supernatant | ◉ | ◉ | ○ | Δ | X | X | X |
| | Precipitate | ◉ | ◉ | ◉ | ◉ | ◉ | ◉ | ◉ |
| Sodium alginate ULV-1 (weight-average molecular weight: 92,000) | Supernatant | ◉ | ◉ | ◉ | ○ | Δ | X | X |
| | Precipitate | ◉ | ◉ | ◉ | ◉ | ◉ | ◉ | ◉ |
| Sodium alginate ULV-L3 (weight-average molecular weight: 54,000) | Supernatant | ◉ | ◉ | ◉ | ○ | Δ | X | X |
| | Precipitate | ◉ | ◉ | ◉ | ◉ | ◉ | ◉ | ◉ |
| Sodium alginate NaAO (weight-average molecular weight: 2,000) | Supernatant | Δ | Δ | X | X | X | X | X |
| | Precipitate | — | — | — | — | — | — | — |

Evaluation:
◉: Harsh/astringent taste is masked and rarely sensed,
○: Harsh/astringent taste is reduced but slightly remains,
Δ: Harsh/astringent taste is slightly masked,
X: No effect,
—: No precipitate.

Effect of alginate on reducing the harsh/astringent taste of protamine varied depending upon the molecular weight differs from the results in the case of polyglutamate. In the case of polyglutamate, the larger the molecular weight, the larger the reducing effect. Whereas, alginate having a high molecular weight (weight-average molecular weight: 1,740,000) had a lower effect of reducing the harsh/astringent taste, than alginate having a low-molecular weight (weight-average molecular weight: 50,000). Furthermore, alginate as low as an alginic oligosaccharide in molecular weight (a weight-average molecular weight: 2,000) did not form a complex. Therefore, the reducing effect was virtually not observed. From these results, to reduce the harsh/astringent taste of protamine by alginate, it was considered that alginate must have a certain size (a polymer size but an oligomer) sufficient to form a complex. Furthermore, as the molecular weight increased, the effect of reducing the harsh/astringent taste decreased. When the molecular weight exceeds 1,000,000, the viscosity of an alginate solution increases. For this, it was conceivably difficult to form a complex with protamine. From these, it was considered that an optimum molecular weight of alginate for forming a complex with protamine must be larger than a weight-average molecular weight of 2,000 and preferably exceeds 5,000. Furthermore, any one of complexes of alginate was tasteless regardless of the molecular weight. Furthermore, in the case of a complex precipitated, since the complex was washed with water, it was possible to remove a salt generated in a mixing process. It was therefore considered that no salty taste was sensed herein although sensed in Example 1 (shown in the results).

Example 7

Effect of Alginate on Reducing the Harsh/Astringent Taste of Protamine Varied Depending Upon the Type of Salt and Ester Thereof With respect to alginate whose effect of reducing the harsh/astringent taste of protamine was confirmed, the effect varying depending upon the type of salt was investigated.

Materials Used:

Protamine: Proserve manufactured by Maruha Nichiro Foods, Inc.

Sodium alginate: ULV-L3 manufactured by KIMICA Corporation

Potassium alginate: K-ULV-L3 manufactured by KIMICA Corporation

Alginate ester: LLV manufactured by KIMICA Corporation

Protamine (1.6 g) was dissolved in distilled water (80 mL) to prepare a 20 mg/mL aqueous protamine solution. Alginate or alginate ester (800 mg) was dissolved in distilled water (20 mL) to prepare a 40 mg/mL solution. Thereafter, the solution was sequentially diluted with distilled water to prepare solutions (20, 15, 10, 7.5, 5 and 2.5 mg/mL). To each of the alginate solutions (0.5 mL), the protamine solution (0.5 mL) was added and stirred, and then subjected to centrifugation (10,000 rpm, 5 minutes). A precipitate was washed with distilled water (1 mL). The supernatant and precipitate of each solution were checked for harsh/astringent taste by a sensory test on a scale of one to three. The results obtained are shown in Table 6.

TABLE 6

The effect of alginate on reducing the harsh/astringent taste of protamine varied depending upon the type of salt and ester thereof

| | | Ratio to protamine | | | | | | |
|---|---|---|---|---|---|---|---|---|
| | | 200% | 100% | 75% | 50% | 37.5% | 25% | 12.5% |
| | | Concentration of substance added (mg/mL) | | | | | | |
| | | 40 | 20 | 15 | 10 | 7.5 | 5.0 | 2.5 |
| Sodium alginate (weight-average molecular weight: 54,000) | Supernatant | ◉ | ◉ | ◉ | ◯ | Δ | X | X |
| | Precipitate | ◉ | ◉ | ◉ | ◉ | ◉ | ◉ | ◉ |
| Potassium alginate (weight-average molecular weight: 51,000) | Supernatant | ◉ | ◉ | ◯ | ◯ | Δ | X | X |
| | Precipitate | ◉ | ◉ | ◉ | ◉ | ◉ | ◉ | ◉ |
| Alginate ester (weight-average molecular weight: 758,000) | Supernatant | X | X | X | X | X | X | X |
| | Precipitate | — | — | — | — | — | — | — |

Evaluation:
◉: Harsh/astringent taste is masked and rarely sensed,
◯: Harsh/astringent taste is reduced but slightly remains,
Δ: Harsh/astringent taste is slightly masked,
X: No effect,
—: No precipitate.

A complex was formed of a potassium salt and protamine similarly to the case of a sodium salt, and the harsh/astringent taste of protamine was reduced. However, when a potassium salt was added in an amount of 75 wt % (3:4) to protamine, the harsh/astringent taste was slightly sensed although the harsh/astringent taste was not sensed in the supernatant in the case of a sodium salt. Thus, the effect of a potassium salt was low compared to a sodium salt. Furthermore, a complex was not formed of an alginate ester (propylene glycol alginate) and protamine and thus, an effect of reducing the harsh/astringent taste of protamine was not confirmed.

Example 8

Figure 2:
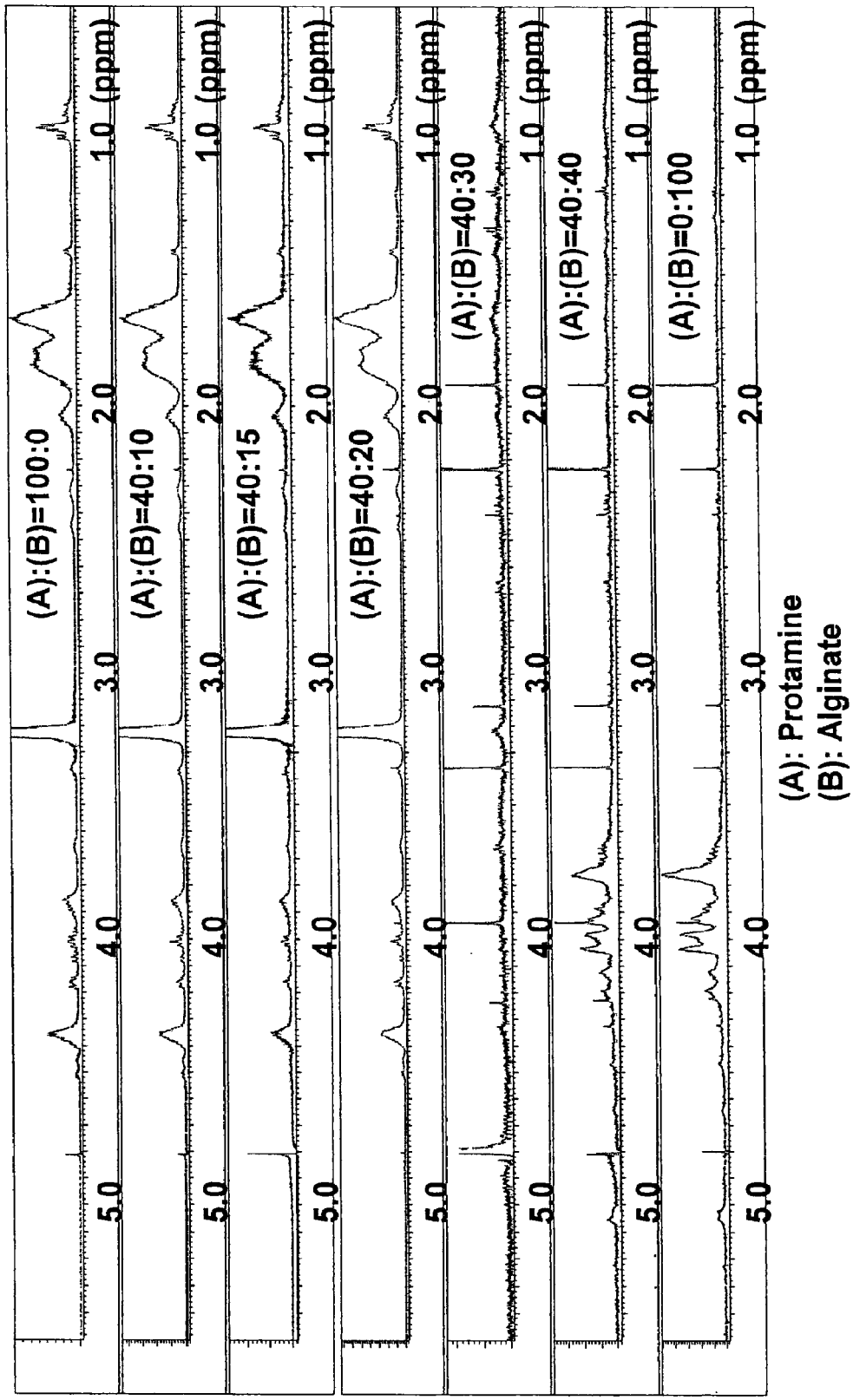
FIG. 2 is a $^1$H NMR spectrum of a complex formed of protamine and alginate.
Figure 3:
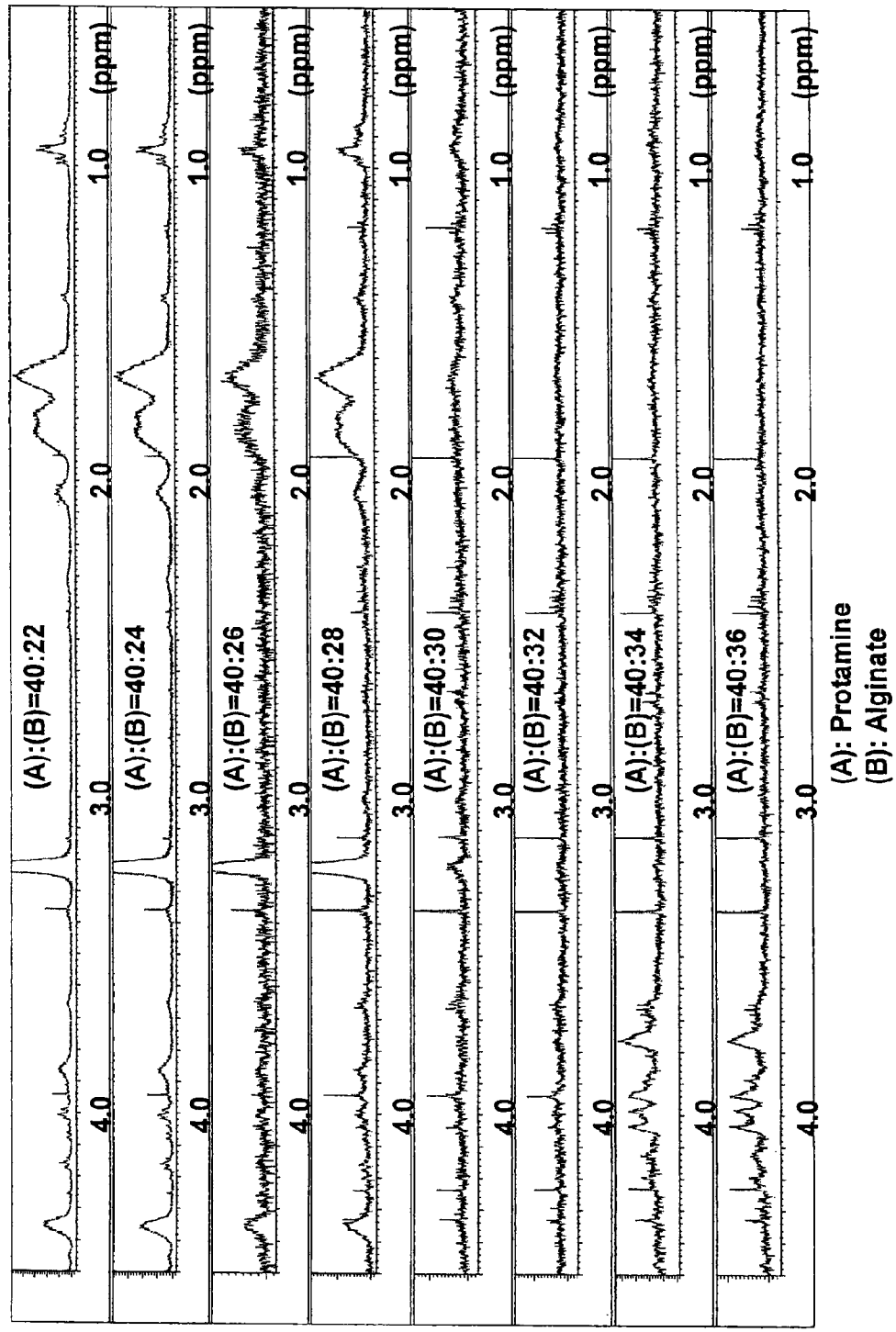
FIG. 3 is a $^1$H NMR spectrum of complex formed of protamine and alginate.

Study on the Ratio of Protamine to Alginate to be Added in Forming a Protamine/Alginate Complex The ratio of protamine to alginate in forming a complex was investigated by NMR measurement.
Materials Used:
Protamine: Proserve manufactured by Maruha Nichiro Foods, Inc.
Alginate: ULV-L3 manufactured by KIM ICA Corporation
Deuterium oxide: Manufactured by Merck KGaA
Protamine (60 mg) and alginate (60 mg) each were dissolved in deuterium oxide (2.5 mL) to prepare 20 mg/mL deuterium oxide solutions. To the protamine deuterium oxide solution (300 μL), the alginate deuterium oxide solution (754 to 300 μL) was added. Further deuterium oxide was added such that a total amount of solution reached 600 μL and stirred, and then subjected to centrifugation (10,000 rpm, 5 minutes). To the supernatant (540 μL), a 0.3 wt % TSP deuterium oxide solution (60 μL) was added and $^1$H NMR measurement was performed. The measurement results thus obtained are shown in FIG. 2 and FIG. 3.

From the results, it was found that when a complex is formed of protamine and alginate, the requisite amount of alginate to protamine is 80 wt % (protamine: alginate=40:32).

Example 9

The Lipase Inhibitory Activity of Complex

Assuming that a complex was orally taken, a treatment was performed in the conditions simulating the stomach, then the lipase inhibitory activity of a complex of protamine was measured.
Materials Used:
Protamine: Proserve manufactured by Maruha Nichiro Foods, Inc.
Alginate: ULV-L3 manufactured by KIM ICA Corporation
Polyglutamate: Polyglutamic acid PGA manufactured by Yakult Pharmaceutical Industry Co., Ltd.
Nucleoprotein: Nucleoprotein P manufactured by Maruha Nichiro Foods, Inc.
Pepsin: Pepsin derived from swine stomach mucous membrane and manufactured by Sigma
Lipase: Lipase derived from swine pancreas and manufactured by Sigma
1. Preparation of Evaluation Sample
To a 20 mg/mL protamine solution (25 μL), a 16 mg/mL alginate solution (25 μL) was added and stirred to prepare an alginate complex suspension. Similarly, to a 20 mg/mL protamine solution (25 μL), a 10 mg/mL polyglutamate solution (25 μL) was added and stirred to prepare a polyglutamate complex suspension. Furthermore, a nucleoprotein (5 mg), which was a complex of protamine and DNA, was added to distilled water (50 μL) and stirred to prepare a suspension. As a control, distilled water (25 μL) was added to each of the 20 mg/mL protamine solution (25 μL), the 16 mg/mL alginate solution (25 μL) and the 10 mg/mL polyglutamate solution (25 μL) to prepare control solutions.
2. Treatment in Gastric Conditions
To each of the complex suspensions (50 μL) thus prepared, a 0.05 M HCl—KCl solution (4,350 μL) was added. Thereafter, the reaction solution was pre-incubated at 37° C. for 5 minutes. To the reactant, an enzyme solution (200 μL), which was prepared by dissolving pepsin (1 mg/mL) in a 0.05 M HCl—KCl solution, was added. After one hour, a 1 M sodium hydrogen carbonate solution (400 μL) was added to neutralize the reaction solution. After neutralization, pepsin was added to the solution. This was used as a solution not treated in the gastric conditions.

3. Evaluation of Lipase Inhibitory Activity

The reaction solution was appropriately diluted with distilled water and subjected to evaluation of a lipase inhibitory activity. More specifically, when the concentration of a substance to be evaluated was 1 μg/mL, the reaction solution (100 μL) was diluted with distilled water (400 μL) (whereas, the nucleoprotein reaction solution (10 μL) was diluted with distilled water (490 μL)). When the concentration of a substance to be evaluated is 0.25 μg/mL, the reaction solution (50 μL) was diluted with distilled water (1 mL). To the diluted reaction solution (10 μL), a substrate solution (140 μL), which was prepared by suspending 4-methylumbelliferyl oleate in a 0.1 M McIlvain buffer solution in a concentration of 31.4 μg/mL, was added and pre-incubated at 37° C. for 5 minutes. To the resultant solution, an enzyme solution (50 μL), which was prepared by suspending lipase in a 0.1 M McIlvain buffer solution in a concentration of 0.24 μg/mL, was added. In this manner, a reaction was initiated. Twenty minutes later, 0.1 M hydrochloric acid (1 mL) was added to terminate the reaction. Each (70 μL) of the reaction solutions was placed in a 96-well black plate. A 0.1 M trisodium citrate solution (140 μL) was added to the wells and fluorescent intensity was measured by a microplate reader (excitation wavelength: 320 nm, measurement wavelength: 450 nm). The test was repeated 5 times. The sample containing no enzyme was treated as a blank and distilled water was treated as a negative control. Inhibition rate was calculated in accordance with the following expression.

Inhibition rate (%)=1−average of sample values (fluorescent intensity−blank)/average of sample values (fluorescent intensity of negative control−blank of negative control)×100

Figure 4:
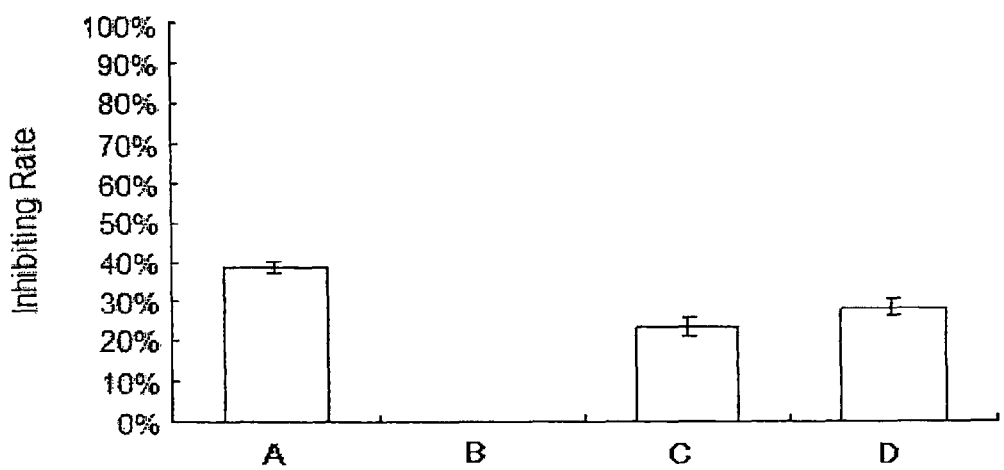
FIG. 4 is a graph showing a lipase inhibitory activity of a complex treated or not treated in the gastric conditions.
Figure 5:
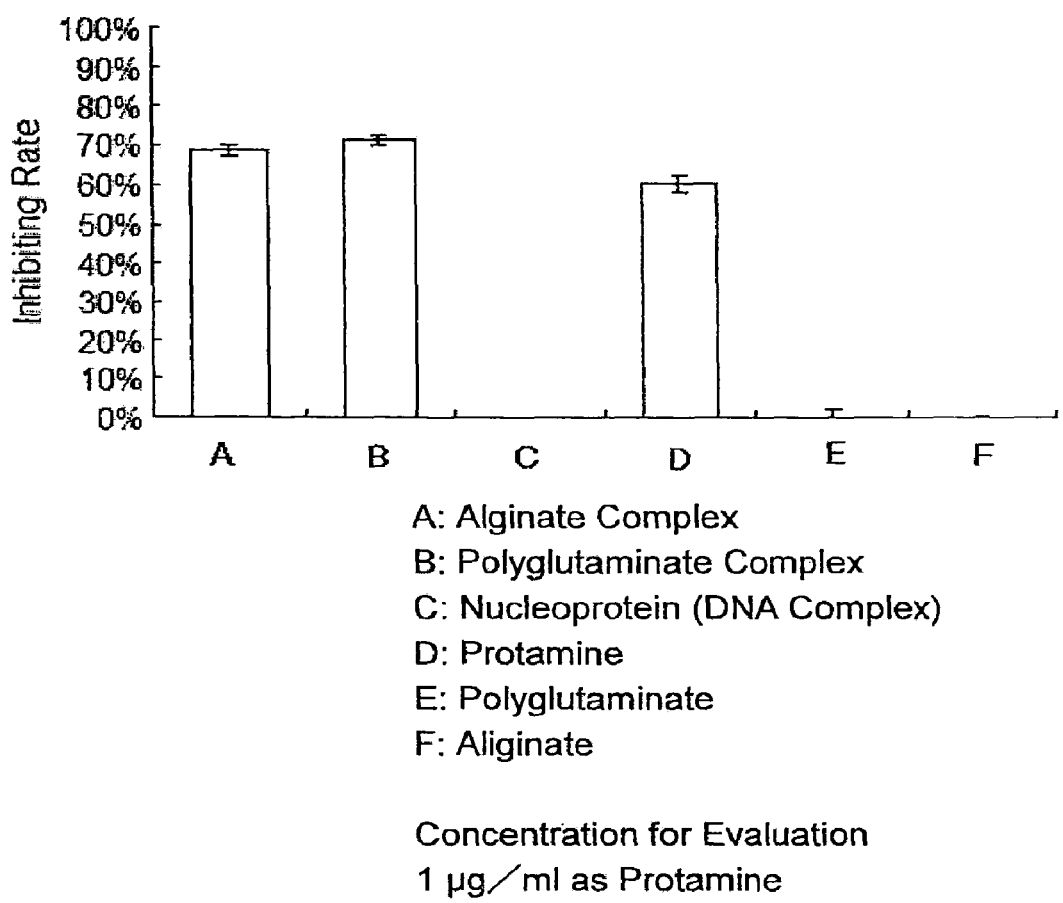
FIG. 5 is a graph showing a lipase inhibitory activity of a complex (treated in the gastric conditions).

The results obtained are shown in FIG. 4 and FIG. 5.

From the results shown in the figures, the following were found. When a treatment was not performed in the gastric conditions, the lipase inhibitory activity of an alginate complex was not confirmed. However, when a treatment was performed in the gastric conditions, lipase inhibitory activity of an alginate complex was confirmed similarly to protamine. Furthermore, it was confirmed that a polyglutamate complex has an inhibitory activity by performing a treatment in the gastric conditions similarly to the case of the alginate complex. However, nucleoprotein, which is a complex of protamine and DNA, did not exhibit the lipase inhibitory activity.

Example 10

Study on the Dissociation of Protamine and Lipase Inhibitory Activity of a Complex Formed of Protamine and Alginates Different in Molecular Weight and Treated in the Gastric Conditions To investigate difference of complexes depending upon the difference in molecular weight of alginate, complexes were formed by using protamine and alginates different in molecular weight and treated in the gastric conditions, and then subjected to $^1$H NMR measurement. Furthermore, the lipase inhibitory activity of the complexes was evaluated.

Materials Used:
Protamine: Proserve manufactured by Maruha Nichiro Foods, Inc.
Alginate: I-8, IL-2, ULV-5, ULV-1, ULV-L3 manufactured by KIM ICA Corporation Pepsin: Pepsin derived from swine stomach mucous membrane and manufactured by Sigma
Lipase: Lipase derived from swine pancreas and manufactured by Sigma The precipitate obtained by the method described in Example 6 was dried to obtain an alginate complex. To the complex (10 mg) or protamine (5 mg), a 0.05 M DCl—KCl deuterium oxide solution (500 μL) was added and pre-incubated at 37° C. for 5 minutes. To the resultant reaction mixture, an enzyme solution (100 μL), which was prepared by dissolving pepsin (1 mg/mL) in a 0.05 M DCl—KCl deuterium oxide solution, was added. In this manner, a reaction was initiated. One hour later, a 1 M deuterium oxide solution of sodium hydrogen carbonate (50 μL) was added to neutralize. After the solution was subjected to centrifugation (5,000 rpm, 5 minutes), an aliquot (560 μL) was taken in a NMR measurement tube. To the tube, a 0.3 wt % TSP deuterium oxide solution (60 μL) serving as a reference substance was added and $^1$H NMR measurement was performed.

Figure 6:
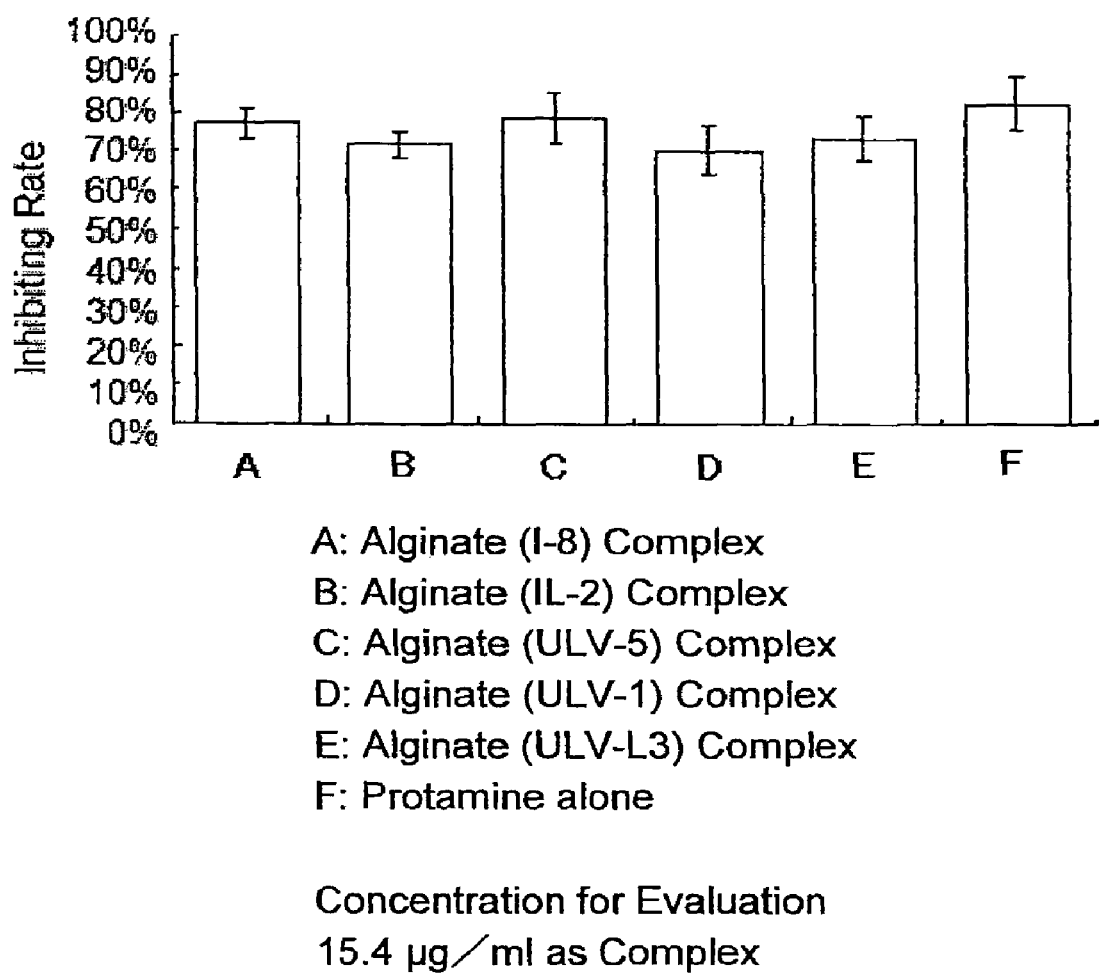
FIG. 6 is a graph showing a lipase inhibitory activity of an alginate complex after treated in the gastric conditions.
Figure 7:
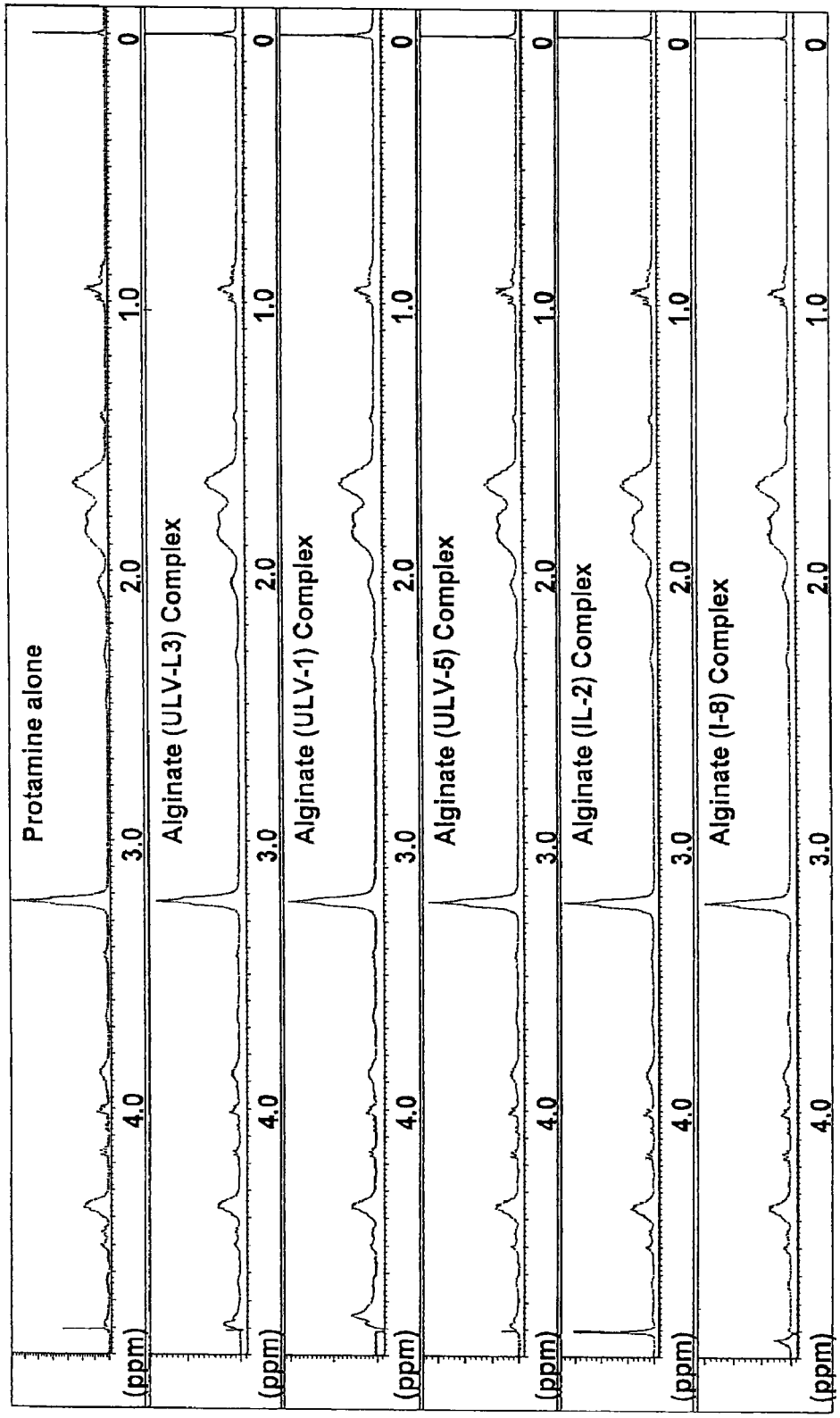
FIG. 7 is a $^1$H NMR spectrum of an alginate complex after treated in the gastric conditions.

Furthermore, using a solution prepared by diluting the reaction solution (20 μL) with distilled water (980 μL), a lipase inhibitory activity was checked in the same manner as in Example 9. The results obtained are shown in FIG. 6 and FIG. 7.

From these results, it was found that protamine was liberated from a complex formed of protamine and alginate regardless of the size of molecular weight by treating the complex in the gastric conditions and exhibited a lipase inhibitory activity.

Example 11

Study on Production of Beverage Using a Complex Formed of Protamine and Alginate With the intention to develop a beverage containing a complex with alginate capable of reducing the harsh/astringent taste of protamine and having a lipase inhibitory activity when treated in the gastric conditions, a production method and stability of the beverage were investigated.

Materials Used:
Protamine: Proserve manufactured by Maruha Nichiro Foods, Inc.
Alginate: ULV-L3 manufactured by KIM ICA Corporation
Thickening agent: soybean polysaccharide SM-700 manufactured by San-Ei Gen F.F.I., Inc.
Malic acid: DL-malic acid manufactured by Riken Kagaku When protamine is orally taken, the effective dose thereof exerting a fat absorption suppressive effect is 0.5 g. Assuming that 0.5 g of protamine is taken from 100 mL of a beverage containing a complex with alginate, a solution was prepared. Furthermore, since a cold beverage containing no preservative must have pH of less than 4.0, a solution rendered to be acidic by use of malic acid was also prepared. Furthermore, since a highly viscous complex was formed immediately upon mixing of a protamine solution and an alginate solution and precipitated, a thickening agent was previously added to the solution to disperse the complex.

To a 15 mg/mL alginate solution (1 mL), each (2 mL) of four thickening agent solutions different in concentration (0, 2, 6 and 10 mg/mL) and each (0.5 mL) of the two malic acid solutions different in concentration (0 and 3.5 mg/mL) were added and stirred, and thereafter, a 40 mg/mL protamine solution (0.5 mL) was added and stirred to obtain good complex suspensions. Each solution was sterilized by heating at 90° C. for 60 minutes and stored at room temperature for a week. The presence or absence of a precipitate was observed and the harsh/astringent taste was checked by a sensory test. The results obtained are shown in Table 7.

TABLE 7

Stability of alginate complex solution

| Concentration of thickening agent | Evaluation item | No addition of malic acid | Addition of malic acid (pH 3.5) |
|---|---|---|---|
| 5 mg/mL | State | No precipitation, white turbidity | No precipitation, white turbidity |
| | Sensory test | ○ | ○ |
| 3 mg/mL | State | Slightly precipitated, white turbidity, precipitate was dispersed after shaking | Slightly precipitated, white turbidity, precipitate was dispersed after shaking |
| | Sensory test | ○ | ○ |
| 1 mg/mL | State | Slightly precipitated, white turbidity, precipitate was dispersed by shaking | Precipitated, thin-white turbidity, precipitate was dispersed after vigorous shaking |
| | Sensory test | ○ | ○ |
| 0 | State | Precipitated, solution is clear, precipitate is not dispersed even by shaking | Precipitated, solution is clear, precipitate is not dispersed even by shaking |
| | Sensory test | ○ | ○ |

Sensory evaluation:
○: Harsh/astringent taste is virtually not sensed,
Δ: Harsh/astringent taste is slightly sensed,
X: Harsh/astringent taste is strongly sensed, In the absence of a thickening agent, an alginate complex would precipitate and would not be dispersed even by shaking. However, an alginate complex was dispersed without precipitating in the presence of a thickening agent of 0.1 wt % or more. An alginate complex was stably dispersed also in acidic conditions. Furthermore, the harsh/astringent taste of protamine was not sensed.

Example 12

Study on the Effect of Powder-Form Alginate or Polyglutamate on Reducing Harsh/Astringent Taste of a Protamine when it is Added and Mixed A complex formed by mixing protamine and solution-state alginate or polyglutamate is expected to exhibit a lipase inhibitory activity by being treated in the gastric conditions, producing fat absorption suppressive effect without the harsh/astringent taste. The present inventors considered that if a complex is formed of protamine, and alginate or polyglutamate at the moment they are orally taken, no harsh/astringent taste will be sensed. Based on the idea, a mixture formed of protamine and a powder of alginate or a polyglutamate was evaluated by a sensory test.

Materials Used:

Protamine: Proserve manufactured by Maruha Nichiro Foods, Inc.

Alginate: ULV-L3 manufactured by KIM ICA Corporation

Polyglutamate: Polyglutamic acid PGA manufactured by Yakult Pharmaceutical Industry Co., Ltd.

To protamine (200 mg), sodium alginate or sodium polyglutamate different in amount (400 mg, 300 mg, 200 mg, 150 mg, 100 mg and 50 mg) was added and sufficiently stirred. Thereafter, the harsh/astringent taste was checked by a sensory test. The results obtained are shown in Table 8.

TABLE 8

The effect of a powder mixture on the reducing harsh/astringent taste of a protamine

| | Ratio to protamine | | | | | |
|---|---|---|---|---|---|---|
| | 200% | 150% | 100% | 75% | 50% | 25% |
| | Addition amount (mg) | | | | | |
| | 400 | 300 | 200 | 150 | 100 | 50 |
| Sodium polyglutamate | ◉ | ◉ | ◉ | ○ | Δ | X |
| Sodium alginate | ◉ | ◉ | ○ | Δ | Δ | X |

Evaluation:
◉: Harsh/astringent taste is masked and rarely sensed,
○: Harsh/astringent taste is reduced but slightly remains,
Δ: Harsh/astringent taste is slightly masked and slightly satisfactory,
X: No effect.

When a complex formed of a powder mixture was compared to a complex formed of a solution mixture, it was confirmed that the addition amounts of alginate and polyglutamate were larger than that of protamine; however, a good effect of reducing the harsh/astringent taste was exerted. In the case of a polyglutamate, the reducing effect was confirmed at an addition amount to protamine of 50 wt % (1:2), and a practical reducing effect was confirmed at an addition amount of 75 wt % (3:4). At an addition amount of 100 wt % (1:1) or more, no harsh/astringent taste was sensed. Furthermore, in the case of alginate, a reducing effect was confirmed at an addition amount to protamine of 50 wt % (1:2) and a practical reducing effect was confirmed at an addition amount of 100 wt % (1:1). At an addition amount of 150 wt % (3:2) or more, no harsh/astringent taste was sensed.

These effects are conceivably produced because a complex is immediately formed by the help of the saliva serving as a medium in the oral cavity, when orally taken. A sufficient effect of reducing the harsh/astringent taste is confirmed just by adding the dry-state components even if a complex is not formed in advance. Cost reduction is expected when a power food and a tablet food, etc. are produced.

Example 13

Study on the Effect of Gum Arabic on Reducing the Harsh/Astringent Taste of Protamine Materials Used:
Protamine: Proserve manufactured by Maruha Nichiro Foods, Inc.
Gum arabic: Arabic cole SS manufactured by Sanei Yakuhin Boueki Co., Ltd.

Protamine (2 g) was dissolved in distilled water (100 mL) to prepare a 20 mg/mL aqueous protamine solution. Furthermore, gum arabic (10 g) was dissolved in distilled water (50 mL) to prepare a 200 mg/mL aqueous solution of gum arabic. An aliquot of the solution was taken and diluted with distilled water to prepare solutions (100, 80, 60, 40 and 20 mg/mL). Assuming that the concentration of protamine to be evaluated is 10 mg/mL (this is a concentration assuming that protamine (0.5 g) is taken from a beverage (50 mL)), a 20 mg/mL aqueous protamine solution (2 mL) was added to the aqueous gum arabic solutions (2 mL) different in concentration. These solutions were evaluated for the harsh/astringent taste by a sensory test. The results obtained are shown in Table 9.

TABLE 9

The effect of gum arabic on reducing the harsh/astringent taste of protamine

| | Concentration of gum arabic solution added (mg/mL) | | | | | |
|---|---|---|---|---|---|---|
| | 200 | 100 | 80 | 60 | 40 | 20 |
| | Ratio to protamine | | | | | |
| | 1,000% | 500% | 400% | 300% | 200% | 100% |
| Concentration of protamine to be evaluated: 10 mg/mL | ◎ | ◎ | ○ | ○ | Δ | X |

Evaluation:
◎: Harsh/astringent taste is masked and rarely sensed,
○: Harsh/astringent taste is reduced but slightly remains,
Δ: Harsh/astringent taste is slightly masked and slightly satisfactory,
X: No effect.

solution of 10 mg/mL in concentration reached 100 wt % (1:1), an effect of reducing the harsh/astringent taste was not confirmed. When the addition amount increased to 200 wt % (2:1), an effect of reducing the harsh/astringent taste was first confirmed. A sufficient effect was confirmed at an addition amount of 400 wt % (4:1). Furthermore, at an addition amount of 500 wt % (5:1), the harsh/astringent taste of protamine was not sensed at all. The addition amount of gum arabic is larger than that of alginate; however, gum arabic does not form a salt such as sodium hydrochloride if added to protamine. Therefore, it is safe to administer gum arabic to a person with a hypertension, who has to avoid intake of sodium chloride. In addition, a suspension of gum arabic has good dispersibility even if a dispersant such as a soybean polysaccharide dispersant is not used. For the reason, more frequent use of gum arabic in a beverage can be greatly expected.

Example 14

When alginate or gum arabic is added to protamine, a complex is formed. The effect of each of them on the fat absorption suppressive effect of protamine was investigated by an animal test.

Materials Used:
Protamine: Proserve manufactured by Maruha Nichiro Foods, Inc.
Alginate: K-ULV-L3 manufactured by KIMICA Corporation
Thickening agent: Soybean polysaccharide SM-700 manufactured by San-Ei Gen F.F.I., Inc.
Gum arabic: Arabic cole SS manufactured by Sanei Yakuhin Boueki Co., Ltd.
Oolong tea: Black oolong tea manufactured by Suntory Holdings Ltd.

1. Preparation of Evaluation Sample:

(1) Sample for control group: Distilled water was filtrated by a membrane filter (DISMIC-13CP, PTFE, φ0.45 μm, ADVANTEC) and used as a test sample for the control group.

(2) Sample for protamine group: Protamine (2.50 g) was dissolved in distilled water (50 mL) filtrated by a membrane filter and used as a test sample for the protamine group.

(3) Sample for alginate mixture group: As a dispersant, soybean polysaccharide (SM-700, 400 mg) was dissolved in distilled water (50 mL) filtrated by a membrane filter to prepare a 0.8% dispersant solution. Protamine (2.00 g) was dissolved with the 0.8% dispersant solution (20 mL) to prepare a protamine solution. To the protamine solution (12.5 mL), an alginate solution (12.5 mL), which was prepared by dissolving alginate (1.60 g) in the 0.8% dispersant solution (20 mL), was added while stirring to prepare a protamine complex suspension and used as a test sample for an alginate complex (mixture) group.

(4) Sample for gum arabic mixture group: Protamine (2.00 g) was dissolved in distilled water (20 mL) to prepare a protamine solution. To the protamine solution (12.5 mL), a gum arabic solution (12.5 mL), which was prepared by dissolving gum arabic (10.0 g) in distilled water (20 mL), was added while stirring to prepare a protamine complex suspension and used as a test sample for a gum arabic mixture group.

(5) Sample for Oolong tea dried product group: Commercially available oolong tea was lyophilized to obtain a dry product. The dry product (2.50 g) was dissolved in distilled water (50 mL) filtrated by a membrane filter, and used as a test sample for the oolong tea dried product group.

2. Animal Test

Evaluation was performed using Male SD rats (6 weeks old, 7 rats per group). The rats were acclimatized for a week and then fasted overnight. To the rats, a test substance (5 mL/kg corresponding to 0.5 g/kg in terms of protamine) was once forcibly administered through mouth. Immediately after that, corn oil (5 mL/kg) was once forcibly administered through mouth. Before the administration and 1.5, 3.0 and 4.5 hours after the administration, blood was taken to obtain the plasma sample of each time point. Using the plasma samples, a blood tri-glyceride level was measured and compared to the control group with respect to blood-level area under the curve (AUC). The results are shown in Table 10.

TABLE 10

|  | AUC relative to control group |
| --- | --- |
| Control group | 100 ± 6% |
| Protamine group | 78 ± 7%[#] |
| Alginate mixture group | 75 ± 6%[#] |
| Gum arabic mixture group | 72 ± 8%[#] |
| Oolong tea dried product group | 78 ± 9% |

[#] t test (p < 0.05)

It was confirmed that the protamine administration group has a significant fat absorption suppressive effect compared to the control group. Furthermore, the same activity as in the protamine group was confirmed in the alginate complex group and the gum arabic mixture group. It was considered that the fat absorption suppressive effect of protamine is not affected by addition of alginate and gum arabic.

What is claimed is:

1. A complex comprising at least one of protamine and salts thereof and at least one of acidic macromolecular substances and gum arabic,
wherein the acidic macromolecular substance is at least one selected from alginic acid, a salt of alginic acid and a monovalent ion, a polyglutamic acid and a salt of a polyglutamic acid.

2. The complex according to claim 1, wherein the acidic macromolecular substance forms a complex with protamine or a salt thereof, thereby producing an effect of reducing harsh/astringent taste of protamine or a salt thereof.

3. A functional food comprising the complex according to claim 1.

4. A fat absorption suppressant comprising the complex according to claim 1.

5. A method of producing a complex comprising at least one of protamine and salts thereof and at least one of acidic macromolecular substances and gum arabic, the method comprising forming a complex by mixing at least one of protamine and salts thereof and at least one of acidic macromolecular substances and gum arabic in an aqueous medium,
wherein the acidic macromolecular substance is at least one selected from alginic acid, a salt of alginic acid and a monovalent ion, a polyglutamic acid and a salt of a polyglutamic acid.

6. The method for producing a complex according to claim 5, further comprising desalting after the complex is formed.

7. The method for producing a complex according to claim 5, wherein the acidic macromolecular substance forms a complex with protamine or the salts thereof, thereby producing an effect of reducing harsh/astringent taste of protamine or a salt thereof.

8. The method for producing a complex according to claim 5, wherein the aqueous medium comprises a dispersant.

9. The method for producing a complex according to claim 8, wherein a concentration of the dispersant is 0.1 wt % to 1 wt %.

10. A method of using at least one of acidic macromolecular substances and gum arabic in order to reduce harsh/astringent taste of at least one of protamine and salts thereof in a food, which comprises producing a complex comprising at least one of protamine and salts thereof and at least one of acidic macromolecular substance and gum arabic in the food, or
adding a complex comprising at least one of protamine and salts thereof and at least one of acidic macromolecular substance and gum arabic to the food,
wherein the acidic macromolecular substance is at least one selected from alginic acid, a salt of alginic acid and a monovalent ion, a polyglutamic acid and a salt of a polyglutamic acid.

11. A method of using at least one of acidic macromolecular substances and gum arabic in order to reduce harsh/astringent taste of at least one of protamine and salts thereof in production of a food comprising at least one of protamine and the salts thereof, which comprises forming a complex comprising at least one of protamine and salts thereof and at least one of acidic macromolecular substance and gum arabic in the food, or
adding a complex comprising at least one of protamine and salts thereof and at least one of acidic macromolecular substance and gum arabic to the food,
wherein the acidic macromolecular substance is at least one selected from alginic acid, a salt of alginic acid and a monovalent ion, a polyglutamic acid and a salt of polyglutamic acid.

12. The method according to claim 10, wherein a ratio of at least one selected from alginic acid, a salt of alginic acid and a monovalent ion, a polyglutamic acid and a salt of a polyglutamic acid relative to at least one of protamine and a salt thereof is 25 wt % to 200 wt %.

13. A powder mixture comprising a powder of at least one of protamine and salts thereof and a powder of at least one of acidic macromolecular substances and gum arabic, wherein the at least one of protamine and the salts thereof and the at least one of the acidic macromolecular substances and gum arabic can form a complex in an aqueous medium,
wherein the acidic macromolecular substance is at least one selected from alginic acid, a salt of alginic acid, a polyglutamic acid and a salt of a polyglutamic acid.

14. The powder mixture according to claim 13, wherein the acidic macromolecular substance forms a complex with at least one of protamine and the salts thereof, thereby producing an effect of reducing harsh/astringent taste of protamine or the salts thereof.

15. The powder mixture according to claim 13, wherein a ratio of the acidic macromolecular substance relative to at least one of protamine and the salts thereof is 25 wt % to 200 wt %.

16. The powder mixture according to claim 13, further comprising a dispersant.

17. A functional food comprising a powder mixture according to claim 13.

18. A fat absorption suppressant comprising the powder mixture according to claim 13 as an active ingredient.

19. The method according to claim 11, wherein a ratio of at least one selected from alginic acid, a salt of alginic acid and a monovalent ion, a polyglutamic acid and a salt of a polyglutamic acid relative to at least one of protamine and a salt thereof is 25 wt % to 200 wt %.

20. The complex according to claim 1, which provides protamine having a lipase inhibitory activity, when the complex is decomposed by pepsin treatment.

21. The method for producing a complex according to claim 5, wherein the complex provides protamine having exhibits a lipase inhibitory activity, when the complex is decomposed by pepsin treatment.

22. The method according to claim 10, wherein the complex provides protamine having a lipase inhibitory activity, when the complex is decomposed by pepsin treatment.

23. The method according to claim 11, wherein the complex provides protamine having a lipase inhibitory activity, when the complex is decomposed by pepsin treatment.

24. The powder mixture according to claim 13, wherein the complex provides protamine having a lipase inhibitory activity, when the complex is decomposed by pepsin treatment.

25. The complex according to claim 1, wherein the salt of alginic acid and a monovalent ion is selected from a sodium salt, a potassium salt, an ammonium salt, a lithium salt, mono-, di- and tri-alkyl amine salts, mono-, di- and tri-hydroxyalkyl amine salts, a guanidine salt, and an N-methyl-glucosamine salt.

26. The method for producing a complex according to claim 5, wherein the salt of alginic acid and a monovalent ion is selected from a sodium salt, a potassium salt, an ammonium salt, a lithium salt, mono-, di- and tri-alkyl amine salts, mono-, di- and tri-hydroxyalkyl amine salts, a guanidine salt and an N-methyl glucosamine salt.

27. The method according to claim 10, wherein the salt of alginic acid and a monovalent ion is selected from a sodium salt, a potassium salt, an ammonium salt, a lithium salt, mono-, di- and tri-alkyl amine salts, mono-, di- and tri-hydroxyalkyl amine salts, a guanidine salt and an N-methyl glucosamine salt.

28. The method according to claim 11, wherein the salt of alginic acid and a monovalent ion is selected from a sodium salt, a potassium salt, an ammonium salt, a lithium salt, mono-, di- and tri-alkyl amine salts, mono-, di- and tri-hydroxyalkyl amine salts, a guanidine salt, and an N-methyl glucosamine salt.

29. A method of producing a complex comprising at least one of protamine and salts thereof and at least one of acidic macromolecular substances and gum arabic, the method comprising:
    forming a complex by mixing at least one of protamine and salts thereof and at least one of acidic macromolecular substances and gum arabic in an aqueous medium containing a dispersant,
    desalting after the complex is formed,
    wherein the acidic macromolecular substance forms a complex with protamine or the salts thereof, thereby producing an effect of reducing harsh/astringent taste of protamine or a salt thereof, and
    wherein the acidic macromolecular substance is at least one selected from alginic acid, a salt of alginic acid and a monovalent ion, a polyglutamic acid and a salt of a polyglutamic acid,
    wherein the salt of alginic acid and a monovalent ion is selected from a sodium salt, a potassium salt, an ammonium salt, a lithium salt, mono-, di- and tri-alkyl amine salts, mono-, di- and tri-hydroxyalkyl amine salts, a guanidine salt, and an N-methyl glucosamine salt.

30. The method for producing a complex according to claim 29, wherein the dispersant is contained in the aqueous medium at a concentration of 0.1 wt % to 1 wt %.

\* \* \* \* \*